US008106060B2

(12) United States Patent
Pfrengle et al.

(10) Patent No.: US 8,106,060 B2
(45) Date of Patent: Jan. 31, 2012

(54) 8-(3-AMINO-PIPERIDIN-1-YL)-XANTHINES, THEIR PREPARATION, AND THEIR USE AS PHARMACEUTICALS

(75) Inventors: Waldemar Pfrengle, Biberach (DE); Peter Sieger, Mittelbiberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 377 days.

(21) Appl. No.: 11/460,996

(22) Filed: Jul. 30, 2006

(65) Prior Publication Data

US 2007/0027168 A1 Feb. 1, 2007

(30) Foreign Application Priority Data

Jul. 30, 2005 (DE) .......................... 10 2005 035 891

(51) Int. Cl.
C07D 473/04 (2006.01)
A61K 31/522 (2006.01)
A61P 3/10 (2006.01)
A61P 3/04 (2006.01)

(52) U.S. Cl. .................................. 514/263.22; 544/269
(58) Field of Classification Search .................. 544/269; 514/263.22
See application file for complete search history.

(56) References Cited

U.S. PATENT DOCUMENTS

| | | | | |
|---|---|---|---|---|
| 2,056,046 | A * | 9/1936 | Fourneau ...................... | 546/197 |
| 2,375,138 | A * | 5/1945 | Salvin et al. ................... | 560/74 |
| 2,629,736 | A * | 2/1953 | Krimmel ........................ | 564/181 |
| 2,730,544 | A * | 1/1956 | Melville et al. ................ | 560/59 |
| 2,750,387 | A * | 6/1956 | Krimmel ........................ | 546/234 |
| 2,928,833 | A | 3/1960 | Leake et al. | |
| 3,174,901 | A | 3/1965 | Sterne | |
| 3,236,891 | A * | 2/1966 | Seemuller ...................... | 564/367 |
| 3,454,635 | A | 7/1969 | Muth | |
| 3,673,241 | A * | 6/1972 | Marxer ........................... | 564/27 |
| 3,925,357 | A * | 12/1975 | Okada et al. ................... | 540/338 |
| 4,005,208 | A | 1/1977 | Bender | |
| 4,061,753 | A | 12/1977 | Bodor et al. | |
| 4,599,338 | A | 7/1986 | Regnier et al. | |
| 4,687,777 | A | 8/1987 | Meguro et al. | |
| 4,873,330 | A * | 10/1989 | Lindholm ....................... | 544/291 |
| 4,968,672 | A | 11/1990 | Jacobson et al. | |
| 5,041,448 | A | 8/1991 | Janssens | |
| 5,051,517 | A | 9/1991 | Findeisen | |
| 5,084,460 | A * | 1/1992 | Munson et al. ................ | 514/282 |
| 5,223,499 | A | 6/1993 | Greenlee | |
| 5,234,897 | A | 8/1993 | Findeisen et al. | |
| 5,258,380 | A | 11/1993 | Janssens | |
| 5,266,555 | A | 11/1993 | Findeisen et al. | |
| 5,300,298 | A | 4/1994 | LaNoue | |
| 5,329,025 | A * | 7/1994 | Wong et al. ................... | 552/10 |
| 5,332,744 | A | 7/1994 | Chakravarty et al. | |
| 5,389,642 | A | 2/1995 | Dorsch | |
| 5,399,578 | A | 3/1995 | Buhlmayer et al. | |
| 5,407,929 | A * | 4/1995 | Takahashi et al. ............. | 514/206 |
| 5,470,579 | A | 11/1995 | Bonte et al. | |
| 5,719,279 | A | 2/1998 | Kuefner-Muhl et al. | |
| 5,728,849 | A | 3/1998 | Bouchard et al. | |
| 5,753,635 | A | 5/1998 | Buckman | |
| 5,958,951 | A * | 9/1999 | Ahrndt et al. .................. | 514/326 |
| 5,965,555 | A | 10/1999 | Gebert et al. | |
| 5,965,592 | A | 10/1999 | Buhlmayer et al. | |
| 6,107,302 | A * | 8/2000 | Carter et al. ............. | 514/263.38 |
| 6,303,661 | B1 | 10/2001 | Demuth | |
| 6,342,601 | B1 | 1/2002 | Bantick | |
| 6,372,940 | B1 * | 4/2002 | Cavazza ........................ | 562/553 |
| 6,548,481 | B1 | 4/2003 | Demuth et al. | |
| 6,579,868 | B1 | 6/2003 | Asano | |
| 6,727,261 | B2 | 4/2004 | Gobbi et al. | |
| 6,784,195 | B2 | 8/2004 | Hale et al. | |
| 6,821,978 | B2 | 11/2004 | Chackalamannil | |
| 6,869,947 | B2 | 3/2005 | Kanstrup | |
| 7,060,722 | B2 | 6/2006 | Kitajima | |
| 7,074,794 | B2 | 7/2006 | Kitajima | |
| 7,074,798 | B2 | 7/2006 | Yoshikawa | |
| 7,074,923 | B2 | 7/2006 | Dahanukar | |
| 7,109,192 | B2 | 9/2006 | Hauel | |
| 7,179,809 | B2 | 2/2007 | Eckhardt | |
| 7,183,280 | B2 * | 2/2007 | Himmelsbach et al. ...... | 514/248 |
| 7,192,952 | B2 | 3/2007 | Kanstrup | |
| 7,217,711 | B2 | 5/2007 | Eckhardt | |
| 7,235,538 | B2 | 6/2007 | Kanstrup et al. | |
| 7,291,642 | B2 | 11/2007 | Kauffmann-Hefner et al. | |
| 7,361,687 | B2 | 4/2008 | Barth et al. | |
| 7,393,847 | B2 | 7/2008 | Eckhardt et al. | |
| 7,407,955 | B2 | 8/2008 | Himmelsbach et al. | |
| 7,432,262 | B2 | 10/2008 | Eckhardt et al. | |
| 7,439,370 | B2 | 10/2008 | Eckhardt | |
| 7,470,716 | B2 | 12/2008 | Eckhardt et al. | |

(Continued)

FOREIGN PATENT DOCUMENTS

CA 1123437 A1 5/1982

(Continued)

OTHER PUBLICATIONS

Busso et al., American Journal of Pathology 166:433-442 (2005).*
"Handbook of Pharmaceutical Salts" (P.H. Stahl, C.G. Wermuth, Wiley-VCH, 2002) p. 61.*
U.S. Appl. No. 11/744,701, Unpublished, filed May 4, 2007, Kohlrausch.
Augustyns, K. et al., The Unique Properties of Dipeptidyl-peptidase IV (DPP IV/CD 26) and the Therapeutic Potential of DPP-IV Inhibitors, Current Medicinal Chemistry, vol. 6, No. 4, 1999, pp. 311-327.
Beljean-Leymarie et al., Hydrazines et hydrazones hétérocycliques. IV. Synthèses de dérivés de l'hydrazine dans la série des imidazo[4,5-d]pyridazinones-4, Can. J. Chem., vol. 61, No. 11, 1983, pp. 2563-2566.
Bollag, R.J. et al; "Osteoblast-Derived Cells Express Functional Glucose-Dependent Insulinotropic Peptide Receptors," Endocrinology, vol. 141, No. 3, 2000, pp. 1228-1235.
Brittain, H.G., "Methods for the Characterization of Polymorphs: X-Ray Powder Diffraction," Polymorphism in Pharmaceutical Solids, 1999, p. 235-238.

(Continued)

Primary Examiner — Mark Berch
(74) Attorney, Agent, or Firm — Michael P. Morris; Timothy X. Witkowski

(57) ABSTRACT

The invention relates to 8-[3-amino-piperidin-1-yl]-xanthines and the physiologically acceptable salts thereof, particularly the hydrochlorides thereof.

21 Claims, 10 Drawing Sheets

U.S. PATENT DOCUMENTS

| | | |
|---|---|---|
| 7,476,671 B2 | 1/2009 | Eckhardt et al. |
| 7,482,337 B2 | 1/2009 | Himmelsbach et al. |
| 7,495,002 B2 | 2/2009 | Langkopf et al. |
| 7,495,003 B2 | 2/2009 | Eckhardt et al. |
| 7,495,005 B2 | 2/2009 | Himmelsbach et al. |
| 7,501,426 B2 | 3/2009 | Himmelsbach et al. |
| 7,550,455 B2 | 6/2009 | Himmelsbach et al. |
| 7,560,450 B2 | 7/2009 | Eckhardt et al. |
| 7,566,707 B2 | 7/2009 | Eckhardt et al. |
| 7,569,574 B2 | 8/2009 | Maier et al. |
| 7,579,449 B2 | 8/2009 | Eckhardt et al. |
| 7,645,763 B2 | 1/2010 | Himmelsbach et al. |
| 7,718,666 B2 | 5/2010 | Boehringer et al. |
| 7,820,815 B2 | 10/2010 | Boehringer et al. |
| 2001/0020006 A1 | 9/2001 | Demuth et al. |
| 2002/0137903 A1 | 9/2002 | Ellsworth et al. |
| 2002/0161001 A1 | 10/2002 | Kanstrup |
| 2002/0169174 A1 | 11/2002 | Chackalamannil et al. |
| 2002/0198205 A1 | 12/2002 | Himmelsbach |
| 2003/0105077 A1 | 6/2003 | Kanstrup et al. |
| 2003/0114390 A1 | 6/2003 | Washburn et al. |
| 2003/0166578 A1 | 9/2003 | Arch et al. |
| 2003/0199528 A1 | 10/2003 | Kanstrup |
| 2003/0224043 A1 | 12/2003 | Appel et al. |
| 2003/0232987 A1 | 12/2003 | Dahanukar et al. |
| 2003/0236272 A1 | 12/2003 | Carr |
| 2004/0023981 A1* | 2/2004 | Ren et al. .................. 514/253.1 |
| 2004/0034014 A1 | 2/2004 | Kanstrup et al. |
| 2004/0063725 A1 | 4/2004 | Barth et al. |
| 2004/0077645 A1 | 4/2004 | Himmelsbach et al. |
| 2004/0082570 A1 | 4/2004 | Yoshikawa |
| 2004/0087587 A1 | 5/2004 | Himmelsbach |
| 2004/0097510 A1* | 5/2004 | Himmelsbach et al. ...... 514/248 |
| 2004/0116328 A1 | 6/2004 | Yoshikawa et al. |
| 2004/0122228 A1 | 6/2004 | Maier |
| 2004/0126358 A1 | 7/2004 | Warne et al. |
| 2004/0138214 A1* | 7/2004 | Himmelsbach et al. ... 514/230.5 |
| 2004/0138215 A1 | 7/2004 | Eckhardt |
| 2004/0166125 A1 | 8/2004 | Himmelsbach |
| 2004/0180925 A1 | 9/2004 | Matsuno et al. |
| 2005/0020574 A1 | 1/2005 | Hauel et al. |
| 2005/0026921 A1 | 2/2005 | Eckhardt |
| 2005/0032804 A1 | 2/2005 | Cypes et al. |
| 2005/0070594 A1 | 3/2005 | Kauschke et al. |
| 2005/0130985 A1 | 6/2005 | Himmelsbach |
| 2005/0143377 A1 | 6/2005 | Himmelsbach et al. |
| 2005/0171093 A1 | 8/2005 | Eckhardt et al. |
| 2005/0187227 A1* | 8/2005 | Himmelsbach et al. . 514/263.22 |
| 2005/0203095 A1 | 9/2005 | Eckhardt |
| 2005/0234108 A1* | 10/2005 | Himmelsbach et al. ...... 514/345 |
| 2005/0234235 A1 | 10/2005 | Eckhardt et al. |
| 2005/0239778 A1 | 10/2005 | Konetzki et al. |
| 2005/0256310 A1 | 11/2005 | Hulin et al. |
| 2005/0261352 A1 | 11/2005 | Eckhardt |
| 2005/0266080 A1 | 12/2005 | Desai et al. |
| 2006/0004074 A1 | 1/2006 | Eckhardt |
| 2006/0039974 A1 | 2/2006 | Akiyama et al. |
| 2006/0047125 A1* | 3/2006 | Leonardi et al. .............. 546/321 |
| 2006/0058323 A1* | 3/2006 | Eckhardt et al. ......... 514/263.22 |
| 2006/0063787 A1 | 3/2006 | Yoshikawa |
| 2006/0079541 A1 | 4/2006 | Langkopf |
| 2006/0094722 A1 | 5/2006 | Yasuda |
| 2006/0100199 A1 | 5/2006 | Yoshikawa et al. |
| 2006/0111379 A1* | 5/2006 | Guillemont et al. .......... 514/275 |
| 2006/0142310 A1* | 6/2006 | Pfrengle et al. .......... 514/263.22 |
| 2006/0154866 A1 | 7/2006 | Chu et al. |
| 2006/0173056 A1 | 8/2006 | Kitajima |
| 2006/0205711 A1 | 9/2006 | Himmelsbach |
| 2006/0205943 A1 | 9/2006 | Dahanukar et al. |
| 2006/0247226 A1 | 11/2006 | Himmelsbach |
| 2006/0270668 A1* | 11/2006 | Chew et al. ................. 514/232.5 |
| 2007/0027168 A1 | 2/2007 | Pfrengle et al. |
| 2007/0060530 A1 | 3/2007 | Christopher et al. |
| 2007/0088038 A1 | 4/2007 | Eckhardt |
| 2007/0093659 A1 | 4/2007 | Bonfanti |
| 2007/0142383 A1 | 6/2007 | Eckhardt |
| 2007/0185091 A1 | 8/2007 | Himmelsbach et al. |
| 2007/0196472 A1* | 8/2007 | Kiel et al. .................... 424/464 |
| 2007/0219178 A1 | 9/2007 | Muramoto |
| 2007/0259900 A1 | 11/2007 | Sieger |
| 2007/0281940 A1 | 12/2007 | Dugi |
| 2007/0299076 A1 | 12/2007 | Piotrowski et al. |
| 2008/0039427 A1* | 2/2008 | Ray et al. .......................... 514/81 |
| 2008/0107731 A1 | 5/2008 | Kohlrausch et al. |
| 2008/0108816 A1 | 5/2008 | Zutter |
| 2008/0249089 A1 | 10/2008 | Himmelsbach et al. |
| 2008/0255159 A1 | 10/2008 | Himmelsbach et al. |
| 2008/0312243 A1 | 12/2008 | Eckhardt et al. |
| 2008/0318922 A1 | 12/2008 | Nakahira et al. |
| 2009/0023920 A1 | 1/2009 | Eckhardt |
| 2009/0088408 A1 | 4/2009 | Meade et al. |
| 2009/0088569 A1 | 4/2009 | Eckhardt et al. |
| 2009/0093457 A1 | 4/2009 | Himmelsbach et al. |
| 2009/0131432 A1 | 5/2009 | Himmelsbach et al. |
| 2009/0137801 A1 | 5/2009 | Himmelsbach et al. |
| 2009/0192314 A1 | 7/2009 | Pfrengle et al. |
| 2009/0325926 A1 | 12/2009 | Himmelsbach |
| 2010/0173916 A1 | 7/2010 | Himmelsbach et al. |
| 2010/0204250 A1 | 8/2010 | Himmelsbach et al. |
| 2011/0046076 A1 | 2/2011 | Eickelmann et al. |
| 2011/0065731 A1 | 3/2011 | Dugi et al. |
| 2011/0092510 A1 | 4/2011 | Klein et al. |
| 2011/0098240 A1 | 4/2011 | Dugi et al. |
| 2011/0112069 A1 | 5/2011 | Himmelsbach et al. |
| 2011/0144083 A1 | 6/2011 | Himmelsbach et al. |
| 2011/0144095 A1 | 6/2011 | Himmelsbach et al. |
| 2011/0190322 A1 | 8/2011 | Klein et al. |
| 2011/0195917 A1 | 8/2011 | Dugi et al. |
| 2011/0206766 A1 | 8/2011 | Friedl et al. |

FOREIGN PATENT DOCUMENTS

| | | |
|---|---|---|
| CA | 2136288 A1 | 5/1995 |
| CA | 2418656 A1 | 2/2002 |
| CA | 2496325 A1 | 3/2004 |
| CA | 2496249 A1 | 4/2004 |
| CA | 2505389 A1 | 5/2004 |
| CA | 2508233 A1 | 6/2004 |
| CA | 2529729 A1 | 12/2004 |
| CA | 2543074 A1 | 6/2005 |
| CA | 2555050 A1 | 9/2005 |
| CA | 2556064 A1 | 9/2005 |
| CA | 2558067 A1 | 10/2005 |
| CA | 2561210 A1 | 10/2005 |
| CA | 2562859 A1 | 11/2005 |
| CA | 2576294 A1 | 3/2006 |
| CA | 2590912 A1 | 6/2006 |
| CA | 2651089 A1 | 11/2007 |
| CN | 101234105 A | 8/2008 |
| DE | 2205815 | 8/1973 |
| DE | 2758025 A1 | 7/1979 |
| DE | 10109021 A1 | 9/2002 |
| DE | 10117803 A1 | 10/2002 |
| DE | 10238243 A1 | 3/2004 |
| DE | 102004019540 A1 | 11/2005 |
| DE | 102004024454 A1 | 12/2005 |
| DE | 102004044221 A1 | 3/2006 |
| EP | 0023032 A1 | 1/1981 |
| EP | 0149578 A2 | 7/1985 |
| EP | 0400974 A2 | 5/1990 |
| EP | 0389282 A2 | 9/1990 |
| EP | 0399285 A1 | 11/1990 |
| EP | 409281 A1 | 1/1991 |
| EP | 0412358 A1 | 2/1991 |
| EP | 443983 A1 | 8/1991 |
| EP | 0524482 A1 | 1/1993 |
| EP | 0657454 A1 | 6/1995 |
| EP | 1054012 A1 | 11/2000 |
| EP | 1333033 | 8/2003 |
| EP | 1338595 A2 | 8/2003 |
| EP | 1406873 A2 | 4/2004 |
| EP | 1500403 A1 | 1/2005 |
| EP | 1514552 A1 | 3/2005 |
| EP | 1557165 A1 | 7/2005 |
| EP | 1537880 A1 | 8/2005 |
| EP | 1586571 A1 | 10/2005 |
| EP | 1760076 | 3/2007 |
| EP | 1829877 A1 | 9/2007 |

| | | | |
|---|---|---|---|
| EP | 1852108 A1 | 11/2007 |
| EP | 2143443 A1 | 1/2010 |
| ES | 385302 A1 | 4/1973 |
| FR | 2707641 A1 | 1/1995 |
| JP | S37-4895 | 6/1962 |
| JP | 2003/300977 | 10/2003 |
| JP | 2006/045156 | 2/2006 |
| KR | 20070111099 A | 11/2007 |
| WO | 91/07945 A1 | 6/1991 |
| WO | 9205175 A1 | 4/1992 |
| WO | 94/03456 A1 | 2/1994 |
| WO | 9402150 A1 | 2/1994 |
| WO | 9609045 A1 | 3/1996 |
| WO | 9636638 A1 | 11/1996 |
| WO | 9723473 A1 | 7/1997 |
| WO | 9807725 | 2/1998 |
| WO | 9811893 A1 | 3/1998 |
| WO | 9822464 A1 | 5/1998 |
| WO | 99/29695 A1 | 6/1999 |
| WO | 0073307 A2 | 12/2000 |
| WO | 0107441 A1 | 2/2001 |
| WO | 0152825 A2 | 7/2001 |
| WO | 0152852 A1 | 7/2001 |
| WO | 0177110 A1 | 10/2001 |
| WO | 0197808 A1 | 12/2001 |
| WO | 02/02560 A2 | 1/2002 |
| WO | 02/14271 A1 | 2/2002 |
| WO | 02/24698 A1 | 3/2002 |
| WO | 02053516 A2 | 7/2002 |
| WO | 02/068420 A1 | 9/2002 |
| WO | 03/004496 A1 | 1/2003 |
| WO | 03000241 A2 | 1/2003 |
| WO | 03002531 A2 | 1/2003 |
| WO | 03/024965 A2 | 3/2003 |
| WO | 03037327 A1 | 5/2003 |
| WO | 03/057200 A2 | 7/2003 |
| WO | 03055881 A1 | 7/2003 |
| WO | 03/104229 A1 | 12/2003 |
| WO | 03099836 A1 | 12/2003 |
| WO | 03106428 A1 | 12/2003 |
| WO | 2004/018467 A2 | 3/2004 |
| WO | 2004/018468 A2 | 3/2004 |
| WO | 2004/028524 A1 | 4/2004 |
| WO | 2004/033455 A2 | 4/2004 |
| WO | 2004/041820 A1 | 5/2004 |
| WO | 2004/046148 A1 | 6/2004 |
| WO | 2004/048379 A1 | 6/2004 |
| WO | 2004/050658 A1 | 6/2004 |
| WO | 2004052362 A1 | 6/2004 |
| WO | 2004065380 A | 8/2004 |
| WO | 2004/096806 A1 | 11/2004 |
| WO | 2004/108730 A1 | 12/2004 |
| WO | 2004/111051 A1 | 12/2004 |
| WO | 2005000846 A1 | 1/2005 |
| WO | 2005000848 A1 | 1/2005 |
| WO | 2005/058901 A1 | 6/2005 |
| WO | 2005049022 A2 | 6/2005 |
| WO | 2005058901 A1 | 6/2005 |
| WO | 2005061489 A1 | 7/2005 |
| WO | 2005/082906 A1 | 9/2005 |
| WO | 2005/085246 A1 | 9/2005 |
| WO | 2005082906 A1 | 9/2005 |
| WO | 2005092870 A1 | 10/2005 |
| WO | 2005092877 A1 | 10/2005 |
| WO | 2005097798 A | 10/2005 |
| WO | 2005116000 A1 | 12/2005 |
| WO | 2005116014 A1 | 12/2005 |
| WO | 2005117861 A1 | 12/2005 |
| WO | 2006005613 A1 | 1/2006 |
| WO | 2006/029769 A1 | 3/2006 |
| WO | 2006036664 A1 | 4/2006 |
| WO | 2006040625 A1 | 4/2006 |
| WO | 2006/048427 A1 | 5/2006 |
| WO | 2006047248 A1 | 5/2006 |
| WO | 2006048209 A1 | 5/2006 |
| WO | 2006/068163 A1 | 6/2006 |
| WO | 2006076231 A2 | 7/2006 |
| WO | 2006135693 A2 | 12/2006 |
| WO | 2006137085 A1 | 12/2006 |
| WO | 2007007173 A2 | 1/2007 |
| WO | 2007/017423 A2 | 2/2007 |
| WO | 2007014886 A1 | 2/2007 |
| WO | 2007014895 A2 | 2/2007 |
| WO | 2007033350 A1 | 3/2007 |
| WO | 2007035355 A2 | 3/2007 |
| WO | 2007041053 A2 | 4/2007 |
| WO | 2007071738 | 6/2007 |
| WO | 2007078726 A2 | 7/2007 |
| WO | 2007093610 A1 | 8/2007 |
| WO | 2007099345 A1 | 9/2007 |
| WO | 2007120702 A2 | 10/2007 |
| WO | 2007120936 A2 | 10/2007 |
| WO | 2007128721 A | 11/2007 |
| WO | 2007128724 A1 | 11/2007 |
| WO | 2007128761 A1 | 11/2007 |
| WO | 2007137107 A2 | 11/2007 |
| WO | 2007148185 A2 | 12/2007 |
| WO | 2007149797 A2 | 12/2007 |
| WO | 2008022267 A2 | 2/2008 |
| WO | WO 2008/017670 A1 | 2/2008 |
| WO | 2008055870 A1 | 5/2008 |
| WO | 2008055940 A2 | 5/2008 |
| WO | 2008070692 A2 | 6/2008 |
| WO | 2008081205 A1 | 7/2008 |
| WO | 2008087198 A1 | 7/2008 |
| WO | 2008093878 A1 | 8/2008 |
| WO | 2008093882 A1 | 8/2008 |
| WO | 2008113000 A1 | 9/2008 |
| WO | 2008131149 A2 | 10/2008 |
| WO | 2009011451 A | 1/2009 |
| WO | 2009022007 A1 | 2/2009 |
| WO | 2009022008 A1 | 2/2009 |
| WO | 2009022010 A1 | 2/2009 |
| WO | 2009024542 A2 | 2/2009 |
| WO | 2009064399 A1 | 5/2009 |
| WO | 2009121945 A2 | 10/2009 |
| WO | 2009123992 A1 | 10/2009 |
| WO | 2009147125 A1 | 12/2009 |
| WO | 2010015664 A1 | 2/2010 |
| WO | 2010018217 A2 | 2/2010 |
| WO | 2010029089 A2 | 3/2010 |
| WO | 2010043688 A1 | 4/2010 |
| WO | 2010072776 A1 | 7/2010 |
| WO | 2010079197 A1 | 7/2010 |
| WO | 2010086411 A1 | 8/2010 |
| WO | 2010092125 A1 | 8/2010 |
| WO | 2010092163 A2 | 8/2010 |
| WO | 2010106457 A2 | 9/2010 |
| WO | 2010147768 A1 | 12/2010 |
| WO | 2011039367 A2 | 4/2011 |
| WO | 2011064352 A1 | 6/2011 |

OTHER PUBLICATIONS

Busso et al., "Circulating CD26 is Negatively Associated with Inflammation in Human and Experimental Arthritis," Am. J. Path., vol. 166, No. 2, Feb. 2005, pp. 433-442.

Caira, M.R., "Crystalline polymorphism of organic compounds" Topics in Current Chemistry, Springer, Berlin, vol. 198, 1998, p. 163-208.

Conarello, S.L. et al; "Mice lacking dipeptidyl peptidase IV are protected against obesity and insulin resistance," PNAS 2003; 100:6825-6830; originally published online May 14, 2003; information current as of Dec. 2006. www.pnas.org/cgi/content/full/100/11/6825.

Deacon, C.F. et al; "Dipeptidyl peptidase IV inhabitation as an approach to the treatment and prevention of type 2 diabetes: a historical perspective;" Biochemical and Biophysical Research Communications (BBRC) 294 (2002) 1-4.

DeMeester, I. et al.; "CD26, let it cut or cut it down", Review: Immunology Today; Aug. 1999, vol. 20, No. 8 pp. 367-375.

Korom, S. et al; Inhibition of CD26/dipeptidyl peptidase IV activity in vivo prolongs cardiac allograft survival in rat recipients[1,2], Transplantation, May 27, 1997, vol. 63, No. 10, pp. 1495-1500.

Pospisilik, et al; Dipeptidyl Peptidase IV Inhibitor Treatment Stimulates β-Cell Survival and Islet Neogenesis in Streptozotocin-Induced Diabetic Rats; Diabetes, vol. 52, Mar. 2003 pp. 741-750.

Rhee et al.: "Nitrogen-15-Labeled Deoxynucleosides. 3. Synthesis of [3-$^{15}$N]-2'3 -Deoxyadenosine" J. Am. Chem. Soc. 1990, 112, 8174-8175.

Sedo, A. et al; "Dipeptidyl peptidase IV activity and/or structure homologs: Contributing factors in the pathogenesis of rheumatoid arthritis?" Arthritis Research & Therapy 2005, vol. 7, pp. 253-269.

Tanaka, S.. et al; "Suppression of Arthritis by the Inhibitors of Dipeptidyl Peptidase IV," In. J. Immunopharmac., vol. 19, No. 1, pp. 15-24, 1997.

Wolff, M.E.: "Burger's Medicinal Chemistry and Drug Discovery" Fifth Edition, vol. 1: Principles and Practice, pp. 975-977, 1994, John Wiley & Sons, Inc.

Zhong, Qing et al; "Glucose-dependent insulinotropic peptide stimulates proliferation and TGF-β release from MG-63 cells," Peptides 24 (2003) 611-616.

Chemical Abstracts Accession No. 1987:95577: Abstract of Romanenko et al., "Synthesis and biological activity of 3-methyl, 7- or 8-alkyl, 7,8-dialkyl, heterocyclic, and cyclohexylaminoxanthines," Farmatsevtichnii Zhurnal, 1986, (Kiev), vol. 5, 1986, pp. 41-44.

Chemical Abstracts Accession No. 106:95577 Romanenko et al., "Synthesis and biological activity of 3-methyl, 7-or 8-alkyl-7,8-dialkyl, heterocyclic, and cyclohexylaminoxanthines," Zaporozh. Med. Institute (1986).

Yoshikawa, Seiji et al.: Chemical Abstract of Japanese Patent No. WO 2003/104229 Preparation of purinone derivatives as dipeptidylpeptidase IV (DPP-IV) inhibitors, 2003.

International Search Report for PCT/EP03/09127 mailed Nov. 28, 2003.

International Search Report for PCT/EP03/12821 mailed Mar. 30, 2004.

International Search Report for PCT/EP03/13648 mailed Apr. 5, 2004.

International Search Report for PCT/EP2007/054270 mailed Aug. 14, 2007.

International Search Report for PCT/EP2007/058181 mailed Nov. 28, 2007.

International Search Report for PCT/EP2007/054204 mailed Aug. 3, 2007.

International Search Report for PCT/EP2007/054201 mailed Aug. 29, 2007.

Patani George A. et al.: "Bioisoterism : A Rational Approach in Drug Design", Chemical Reviews, 1996, vol. 96, No. 8, pp. 3147-3176.

Cygankiewicz, Andrzej et al., Investigations into the Piperazine Derivatives of Dimethylxanthine: Acta Polon. Pharm. [Papers of Polish Pharmacology], XXXOV, No. 5, pp. 607-612, 1977.

Januvia; Patient Information; Oct. 2007.

Zejc, Alfred et al; Badania Nad Piperazynowymi Pochodnymi Dwumetyloksantyn; Acta Polon. Pharm. XXXV. Nr 4, 1976, pp. 417-421.

Zhong, Qing et al; "Glucose-dependent insulinotropic peptide stimulates proliferation and TGF-β release from MG-63 cells," Peptides 24 (2003) 611-616.

Abstract in English for German DE2205815, 1972.

Abstract in English for German EP0023032, 1981.

Abstract in English, for KR20070111099, Nov. 11, 2007.

Ahren B: "DPP-4 inhibitors", Best practice and research in clinical endocrinology and metabolism—New therapies for diabetes 200712 GB LNKD—DOI:10.1016/J. Beem.2007.07.005, vol. 21, No. 4, Dec. 2007, pp. 517-533.

Auger!, D.J. "Discovery and Preclinical Profile of Saxagliptin (GMB-477118): A Highly Potent, Long-Acting, Orally Active Dipeptidyl Peptidase IV Inhibitor for the Treatment of Type 2 Diabetes". Journal Med. Chem, 2005, vol. 48, No. 15, p. 5025-5037.

Aulinger, B.A. et al., "Ex-4 and the DPP-IV Inhibitor Vildagliptin have Additive Effects to Suppress Food Intake in Rodents". Abstract No. 1545-P, 2008.

Balaban, Y.H.et al., "Dipeptidyl peptidase IV (DDP IV) in NASH patients" Annals of Hepatology, vol. 6, No. 4, Oct. 1, 2007, pp. 242-250, abstract.

Balkan, B. et al, "Inhibition of dipeptidyl peptidase IV with NVP-DPP728 increases plasma GLP-1 (7-36 amide) concentrations and improves oral glucose tolerance in obses Zucker rates". Diabetologia, 1999, 42, p. 1324-1331.

Brazg, R. et al: "Effect of adding sitagliptin, a dipeptidyll peptidase-4 inhibitor, to metformin on 24-h glycaemic control and beta-cell function in patients with type 2 diabetes." Diabetes, Obesity and Metabolism, Mar. 2007, vol. 9, No. 2, Mar. 2007 pp. 18-193.

Bundgaard, H. "Design of prodrugs: Bioreversible derivatives for various functional groups and chemical entities". Royal Danish School of Pharmacy, 1985, p. 1-92.

Chemical Abstract. EP412358, 1991:185517, Findeisen. 1991.

Chemical Abstract: FR2707641, 1995:543545, Dodey. 1995.

Chemical Abstracts Accession No. 106:95577 Romanenko et al., "Synthesis and Biological Activity of 3-Methyl, 7- or 8-alkyl-7,8dialkyl, heterocyclic, and cyclohexylaminoxanthines," Zaporozh. Med. Institute (1986).

Clinical Trials. "View of NCT00601250 on 1008-01-25: *Efficacy and Safety of BI 1356* vs *Placebo* added to Metformin Background Therapy in Patients with Type 2 Diabetes" Clinical Trials. Gov Archive, [Online] 25 Jan. 2008 URL:http://clinicaltrials.gov/archive/NCT00601250/2008_01_25 [retrieved on 2009-02-27].

Clinical Trials. NCT00622284. "Efficacy and safety of BI 1356 in combination with metformin in patients with type 2 diabetes" ClinicalTrials.gov (Online) No. NCT00622284, Feb. 13, 2008, p. 1-5, URL:http://clinicaltrial.govict2/show/.

Combs, D. W. et al., "Phosphoryl Chloride Induced Ring Contraction of 11,4-Benzodiazepinones to Chloromethylquinazolines". J. Heterocyclic Chemistry, BD. 23, 1986, p. 1263-1264.

Conarello, S.L. et al., "Mice lacking dipeptidyl peptidase IV are protected against obesity and insulin resistance". PNAS, May 27, 2003, vol. 100, No. 11, p. 6825-6830.

Dave, K.G. et al., "Reaction of Nitriles under Acidic Conditions, Part I. A General Method of Synthesis of Condensed Pyrimidines", J. Heterocyclic Chemistry, BD, 17, 1, ISSN 0022-152X,Nov. 1980, p. 1497-1500.

Deacon, C.F., et al. Inhibitors of dipeptidyl peptidase IV: A novel approach for the prevention and treatment of Type 2 diabetes? Expert Opinion on Investigational Drugs, Sep. 2004, vol. 13, No. 9, p. 1091-1102.

Dugi, K.A. et al., "Bi 1356, a novel xanthine-based DPP-IV inhibitor, exhibits high potency with a wide therapeutic window and significantly reduces postprandial glucose excursions after an oGTT". Diabetologia, vol. 50, No. Suppl 1, Sep. 2007, p. S367, and 43rd Annual Meeting of the European Association for the Study of Diabetes; Amsterdam, Netherlands, Sep. 18-21, 2007.

Eckhardt Matthias et al: 8-(3-(R)-aminopiperidin-1-yl)-7-but-2-yny 1-3-methyl-1-(4-methyl-quina zolin-2-ylmethyl)-3,7-dihydropurine-2,6-dione (BI 1356), a highly potent, selective, long-acting, and orally bioavailable DPP-4 inhibitor for the treatment of type 2 diabetes: Journal of Medicinal Chemistry, American Chemical Society. Washington.; US, vol. 50, No. 26, Dec. 1, 2007, p. 6450-6453.

Eckhardt, M. et al., "3,5-dihydro-imidazo[4,5-d]pyridazin-4-ones: a class of potent aDPP-4 inhibitors" Bioorganic & Medicinal Chemistry Letters, Pergamon, Elsevier Science, GB, vol. 18, No. 11, Jun. 1, 2008, pp. 3158-3162, XP022711188.

Elrishi M A et al: "The dipeptidyl-peptidase-4 (D::-4) inhibitors: A new class of oral therapy for patients with type 2 diabetes mellitus" Practical Diabetes International Chichester, vol. 24, No. 9, 1 Nov. 2007 pp. 474-482.

Florez, Jose C., et al., "TCF7L2 Polymorphisms and progression to diabetes in the diabetes prevention program". New England Journal of Medicine, MA Medical Society, vol. 355, No. 2, Jul. 20, 2006, p. 241-250.

Gallwitz, B. et al., "Saxagliptin, a dipeptidyl peptidase IV inhibitor for the treatment of type 2 diabetes". IDRUGS, vol. 11, No. 12, Dec. 2008, p. 906-917.

Garber, A.J. et al., "Update: Vildaglitin for the treatment of Type 2 diabetes" Expert Opinion on Investigational Drugs, 200801GB, vol. 17, No. 1, Jan. 2008, p. 105-113.

Garcia-Soria, et al., "The dipeptidyl peptidase-4 inhibitor PHX1149 improves blood glucose control in patents with type 2 diabetes mellitus". Diabetes, Obesity and Metabolism, Apr. 2008, vol. 10, No. 4, p. 293-300.

Gennaro, Alfonso, R; Remington: The Science and Practice of Pharmacy: Oral Solid Dosage Forms; Mack Publishing Company, Philadelphia, PA (1995) vol. II, 19th Edition, Ch. 92 pp. 1615-1649.

Giron, D.; Thermal Analysis and Calorimetric Methods in the Characterisation of Polymorphs and Solvates; Thermochimica Acta (1995) vol. 248 pp. 1-59.

Graefe-Mody et al., "The novel DPP-4 inhibitor" Diabetes, (online) 2008, XP002561421 http://professional.diabetes.org/content/posters/2008/p553-p.pdf.

Greene, T.W, et al., "Protection for the Amino Group". Protective Groups in Organic Synthesis, 3rd edition, 1999, p. 494-653.

Gwaltney, S. "Medicinal Chemistry Approaches to the Inhibition of Dipeptidyl Peptidase IV", Current Topics in Medicinal Chemistry, 2008, 8, p. 545-1552.

He. Y. L. "The influence of hepatic impairment on the pharmacokinetics f the dipeptidyl peptidase IV (DPP-4) inhibitor vildagliptin" European Journal of Clinical Pharmacology, vol. 63, No. 7, May 8, 2007, p. 677-686.

Huettner Silks et al: "BI 1356, a novel and selective xanthine based DPP-IV inhibitor, demonstrates good safety and tolerability with a wide therapeutic window" Diabetes< American Diabetes Association, US, vol. 56, No. Suppl 1, Jun. 1, 2007, p. A156.

International Search Report and Written Opinion for PCT/EP2009/061659 mailed Mar. 9, 2010.

International Search Report and Written Opinion for PCT/EP2009/063511 mailed Feb. 26, 2010.

International Search Report and Written Opinion for PCT/EP2010068349 mailed Feb. 4, 2011.

International Search Report for PCT/EP2006/064657 mailed Nov. 2, 2006.

International Search Report for PCT/EP2010/051093 mailed Jul. 14, 2010.

International Search Report for PCT/EP2010/064691 mailed Jan. 20, 2011.

Kanada, S. et al., "Safety, tolerability, pharmacokenetics and pharmacodynamics of multiple doses of BI 1356 (proposed tradename ONDERO), a dipeptidyl peptidase 4 inhibitor, in Japanese patients with type 2 diabetes" Diabetes, vol. 57, No. Suppl. 1, Jun. 2008, p. A158-A159 and 68th Annual Meeting of the American Diabetes Association: San Francisco, CA , Jun. 6-10, 2008.

Kim, D. et al., "(2R)-4-Oxo-4-(3-(Trifluoremethyl)-5,6-dihydro[1,2,4]triazolo[4,3-a]pyrazin-7(8H)-yl]-1-(2,4,5-trifluorophenyl)butan-2-amine: A Potent, Orally Active Dipeptidyl Peptidase IV inhibitor for the Treatment of Type 2 Diabetes." Journal Med. Chem, 2005, 48, p. 141-151.

Lambier, A.M. et al., Dipeptidyl-Peptidase IV from Bench to Bedside: An Update on Structural Properties, Functions, and Clinical Aspects of the Enzyme DPP IV. Critical Reviews in Clinical Laboratory Sciences, 2003, 40(3), p. 209-294.

March, J. "Advanced Organic Chemistry: Reactions, Mechanisms, and Structure". Fourth Edition, 1992, pp. 652-653.

Mendes, F.D, et al. "Recent advances in the treatment of non-alcoholic fatty liver disease". Expert Opinion on Investigational Drugs, vol. 14, No. 1, Jan. 1, 2005, p. 29-35.

O'Farrell, et al., "Pharmacokinetic and Pharmacodynamic Assessments of the Dipeptidyl Peptidase-4 Inhibitor PHX1149: Double-Blind, Placebo-controlled, Single-and Multiple-Dose Studies in Healthy Subjects". Clinical Therapeutics, Excerpta Medica, Princeton, NJ, vol. 29, No. 8, 2007, p. 1692-1705.

Pei, Z.: "From the bench to the bedside: Dipeptidyl peptidase IV inhibitors, a new class of oral antihyperglycemic agents" Current Opinion in Drug Discovery and Development, Current Drugs, London, GB vol. 11, No. 4, Jul. 1, 2008 pp. 512-532.

Priimenko, B. A., et al; Synthesis and Pharmacological Activity of Derivates of 6,8-Dimethyl Imidazol(1,2-f) Xanthine-(Russ.); Khimiko-Farmatsevticheskii zhurnal (1984) vol. 18, No. 12 pp. 1456-1461.

Rosenstock, et al., "Efficacy and tolerability of initial combination therapy with vildagliptin and pioglitazone compared with component montherapy in patients with type 2 diabetes". Diabetes, Obesity and Metabolism, Mar. 2007, vol. 9, No. 2, p. 175-185.

Salomon, J., et al; Ultraviolet and g-Ray-Induced Reactions of Nucleic Acid Constituents. Reactions of Purines with Amines; Photochemistry and Photobiology (1974) vol. 19 pp. 21-27.

Sathananthan, A., et al., "Personalized pharmacotherapy for type 2 diabetes mellitus". Personalized Medicine 2009 Future Medicine Ltd, vol. 6, No. 4, Jul. 2009, p. 417-422.

Sauer, R, et al. "Water-soluble phosphate prodrugs of 1-Propargyl-7-styrylxanthine derivatives, A2A-selective adenosine receptor antagonists". Journal Med. Chem., vol. 43, Issue 3, Jan. 2000, p. 440-448.

Schwartz, M. S. et al., "Type 2 Diabetes Mellitus in Childhood: Obesity and Insulin Resistance". JAOA Review Article, vol. 108, No. 9, Sep. 2008, p. 518.

Scientific Discussion: "Eucreas. Scientific discussion". Online Oct. 2007, p1-27, URL:http://www.emea.europa.eu/humandocs/PDFs/EPAR/eucreas/H-807-en6.pdf. see point 2. quality aspects pp. 2-4. (EMEA).

Tamm, E, et al., "Double-blind study comparing the immunogenicity of a licensed DTwPHib-CRM197 conjugate vaccine (Quattvaxem TM) with three investigational, liquid formulations using lower doses of Hib-CRM197 conjugate". Science Direct, Vaccine, Feb. 2005, vol. 23, No. 14, p. 1715-1719.

Thomas, L, et al: "BI 1356, a novel and selective xanthine beased DPP-IV inhibitor, exhibits a superior profile when compared to sitagliptin and vildagliptin." Diabetologoa, vol. 50, No. Suppl. 1, Sep. 2007, p. S363.

Thomas, Leo et al: " (R)-8-(3-Amino-piperidin-1-y1)-7-but-2-yny1-3-methyl-1-(4-methyl-quinazolin-2-ylmethyl)-3,7-dihydro-purine-2,6-dione (BI 1356), a Novel Xanthine-Based Dipeptidyl Peptidase 4 Inhibitor, Has a Superior Potency and Longer Duration of Action Compared with Other Dipeptidyl Peptidase-4 Inhibitors" Journal of Pharmacology and Experimental Therapeutics, American Socity for Therapeutics, US, vol. 325, No. 1, 1 Apr. 2008, pp. 175-182 abstract p. 177, col. 2, paragraph 1 table 1 p. 1B1, col. 2, last paragraph—p. 182, col. 1.

U.S. Appl. No. 12/724,653, filed Mar. 16, 2010—Xanthine Derivatives, the Preparation Thereof and Their Use as Pharmaceutical Compositions. Inventor: Frank Himmelsbach, et al.

U.S. Appl. No. 12/767,855, filed Apr. 27, 2010—Xanthine Derivatives, the Preparation Thereof and Their use as Pharmaceutical Compositions. Inventor: Frank Himmelsbach, et al.

Villhauer, E.B., "1-[[3-Hydroxy-1-adamantyl)pamino]acetyl]-1-cyano-(S)-pyrrolidine: A Potent, Selective, and Orally Bioavailable Dipeptidyl Peptidase IV Inhibitor with Antihyperglycemic Properties" Journal Med. Chem, 2003, 46, p. 2774-2789.

Villhauer, E.B., et al., "1-{2-{5-Cyanopyridin-2-yDamino)-ethylamino}acetyl-1-1(S)-pyrrolidine-carbonitrile: A Potent, Selective, and Orally Bioavailable Dipeptidyl Peptidase IV Inhibitor with Antihyperglycemic Properties". Journal of Medical Chemistry, 2002, vol. 45, No. 12, p. 2362-2365.

Wang Y et al: "BI-1356. Dipeptidyl-peptidase IV inhibitor, antidiabetic agent" Drugs of the Future, Prous Science, ES,vol. 33, No. 6, 1 Jun. 208, pp. 473-477.

White, J.R., "Dipeptidyl Peptidase-IV Inhibitors: Phamacological Profile and Clinical Use". Clinical Diabetes, vol. 26, 2008, p. 53-57.

Wikipedia, Annulation. Jun. 23, 2008, http://en.wikipedia.org/wiki/Annelation.

Williams-Herman, D. et al., "Efficacy and safety of initial combination therapy with sitagliptin and metformin in patients with type 2 diabetes: a 54-week study". Current Medical Research and Opinion, Informa Healthcare, GB, vol. 25, No. 3, Jan. 2009, p. 569-583.

World Health Organization (WHO). Addendum 1 to "The use of stems in the selection of International Nonproprietary names (INN) for pharmaceutical substances"" Online Jun. 19, 2007, pp. 1-3, retrieved from URL: http://www.who.int/medicindedocs/index/assoc/s1414e/s1414e.pdf.

Yasuda, et al. "E3024 3-but-2-yny1-5-methyl-2-piperazin-1-y1-3,5-dihydro-4H-imidazol [ 4,5-d]pyridazin-4-one tosylate, is a move, selective and competitive dipeptidyl peptidase-IV inhibitor". European Journal of Pharmacology, vol. 548, No. 1-3, Oct. 24, 2006, p. 181-187. Abstract.

Zimmer et al; Synthesis of 8-Substituted Xanthines and their Oxidative Skeleton Rearrangement to 1-Oxo-2,4,7,9-tetraazaspiro[4,5]dec-2-ene-6,8,10-triones; Euripean Journal Organic Chemistry (1999) vol. 9 pp. 2419-2428.

X-Ray Diffraction. The United States Pharmacopeia, 2002, USP 25 NF20, p. 2088-2089.

Clinical Trials. View of NCT00730275 updated on Aug. 7, 2008. "A study to assess the pharmacokinetics, safety and tolerability of Sitagliptin in adolescents". http://clinicaltrials.gov/archive/NCT00730275/2008_08_07 .

Clinical Trials: NCT00309608. Efficacy and safety of BI 1356 in combination with metformin in patients with type2 diabetes. Boehringer Ingelheim Pharmaceuticals, Jan. 27, 2009. Clinical Trials.gov. http://clinicaltrials.gov/archive/NCT00309608/2009_01_27.

Clinical Trials: NCT00602472. "BI 1356 in combination withe metformin and a sulphonylurea in Type 2 Diabetes". DrugLib.com, Nov. 3, 2008. http://www.druglib.com/trial/08/NCT00309608.html.

Clinical Trials: NCT00622284. Efficacy and Safety of BI 1356 in Combination with Metformin in Patients with Type 2 Diabetes. Boehringer Ingelheim Pharmaceuticals, Aug. 2008. http://clinicaltrials.gov/archive/NCT00622284/2010_01_13.

Clinical Trials: NCT00798161. "Safety and efficacy of BI 1356 Plus Metformin in Type 2 Diabetes, Factorial Design". Clinical Trials.gov archive. A Service of the U.S> National Institutes of Health. Nov. 24, 2008, p. 1-3. http://clinicaltrials.gov/archive/NCT00798161/2008_11_24.

Merck: "Initial Therapy with Janumet (sitagliptin/metformin) provided significantly greater blood sugar lowering compared to metformin alone in patients with type 2 diabetes". Webwire.com, Jun. 8, 2009, p. 1-4. http://www.webwire.com/ViewPressRel.asp?aId=96695.

Augusti, D.V. et al., "Quantitative determinatio of the enantiomeric composition of thalidomide solutions by electrospray ionizatio tandem mass spectrometry". Chem Comm, 2002, p. 2242-2243.

International Search Report and Written Opinion for PCT/EP2006/064657 mailed Nov. 2, 2006.

Jones, R.M. et al., "GPR119 agonists for the treatment of type 2 diabetes". Expert Opinion on Therapeutic Patents 2009 Informa Healthcare for GBR LNKSD—DOI: 10.1517/13543770903153878, vol. 19, No. 10, Oct. 2009, p. 1339-1359.

* cited by examiner

8-(3-AMINO-PIPERIDIN-1-YL)-XANTHINES, THEIR PREPARATION, AND THEIR USE AS PHARMACEUTICALS

BACKGROUND OF THE INVENTION

1. Field of the Invention

The present invention relates to new substituted xanthines of formula

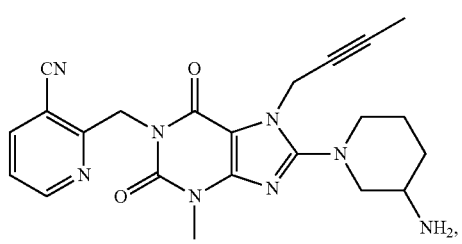

(I)

the tautomers, the enantiomers, the mixtures thereof, the salts thereof and the hydrates thereof, particularly the physiologically acceptable salts thereof with inorganic or organic acids, such as hydrochlorides, for example, which have valuable pharmacological properties, particularly an inhibiting effect on the activity of the enzyme dipeptidylpeptidase-IV (DPP-IV), the preparation thereof, the use thereof for preventing or treating illnesses or conditions connected with an increased DPP-IV activity or capable of being prevented or alleviated by reducing the DPP-IV activity, particularly type I or type II diabetes mellitus, the pharmaceutical compositions containing a compound of general formula (I) or a physiologically acceptable salt thereof and processes for the preparation thereof.

2. Description of the Prior Art

Xanthine derivatives with an inhibitory effect on DPP-IV are already known from WO 02/068420, WO 02/02560, WO 03/004496, WO 03/024965, WO 04/018468, WO 04/048379, JP 2003300977 and EP 1 338 595, which references are incorporated herein by reference in their entireties.

SUMMARY OF THE INVENTION

The aim of the invention is to provide new compounds of formula I, particularly salts with advantageous properties for pharmaceutical use.

In addition to its actual efficacy for the desired indication, an active substance must also meet other requirements in order to be capable of being used as a pharmaceutical composition. These parameters are to a large extent connected with the physicochemical nature of the active substance.

Without being restricted thereto, examples of these parameters are the stability of effect of the starting substance under different ambient conditions, stability in the course of the preparation of the pharmaceutical formulation and stability in the final compositions of the pharmaceutical preparation. The pharmaceutical active substance used to prepare the pharmaceutical compositions should therefore have high stability, which should also be guaranteed even under different environmental conditions. This is absolutely essential to prevent the use of pharmaceutical compositions which contain, in addition to the active substance itself, breakdown products thereof, for example. In such cases the content of active substance found in the pharmaceutical formulations might be less than specified.

The absorption of moisture reduces the content of pharmaceutically active substance as a result of the increased weight caused by the uptake of water. Pharmaceutical compositions with a tendency to absorb moisture have to be protected from moisture during storage, e.g. by the addition of suitable drying agents or by storing the drug in an environment where it is protected from moisture. In addition, the uptake of moisture may reduce the content of pharmaceutically active substance during manufacture if the pharmaceutical substance is exposed to the environment without being protected from moisture in any way. Preferably, therefore, a pharmaceutically active substance should be only slightly hygroscopic.

As the crystal modification of an active substance is important to the reproducible active substance content of a preparation, there is a need to clarify as far as possible any existing polymorphism of an active substance present in crystalline form. If there are different polymorphic modifications of an active substance, care must be taken to ensure that the crystalline modification of the substance does not change in the pharmaceutical preparation later produced from it. Otherwise, this could have a harmful effect on the reproducible potency of the drug. Against this background, active substances which are characterised by only slight polymorphism are preferred.

Another criterion which may be of exceptional importance under certain circumstances depending on the choice of formulation or the choice of manufacturing process for the formulation is the solubility of the active substance. If for example pharmaceutical solutions are prepared (e.g. for infusions), it is essential that the active substance should be sufficiently soluble in physiologically acceptable solvents. It is also very important for drugs which are to be taken orally that the active substance should be sufficiently soluble.

The problem of the present invention is to provide a pharmaceutically active substance which not only is characterised by high pharmacological potency but also satisfies the above-mentioned physicochemical requirements as far as possible.

Surprisingly it has been found that the salts of the compound of formula I with hydrochloric acid, the enantiomers thereof, the mixtures and the hydrates thereof satisfy this requirement. Particularly suitable for the purposes of this invention are the mono- and dihydrochloride as well as the enantiomers thereof, the mixtures and the hydrates thereof.

DETAILED DESCRIPTION OF THE INVENTION

Figure 1:
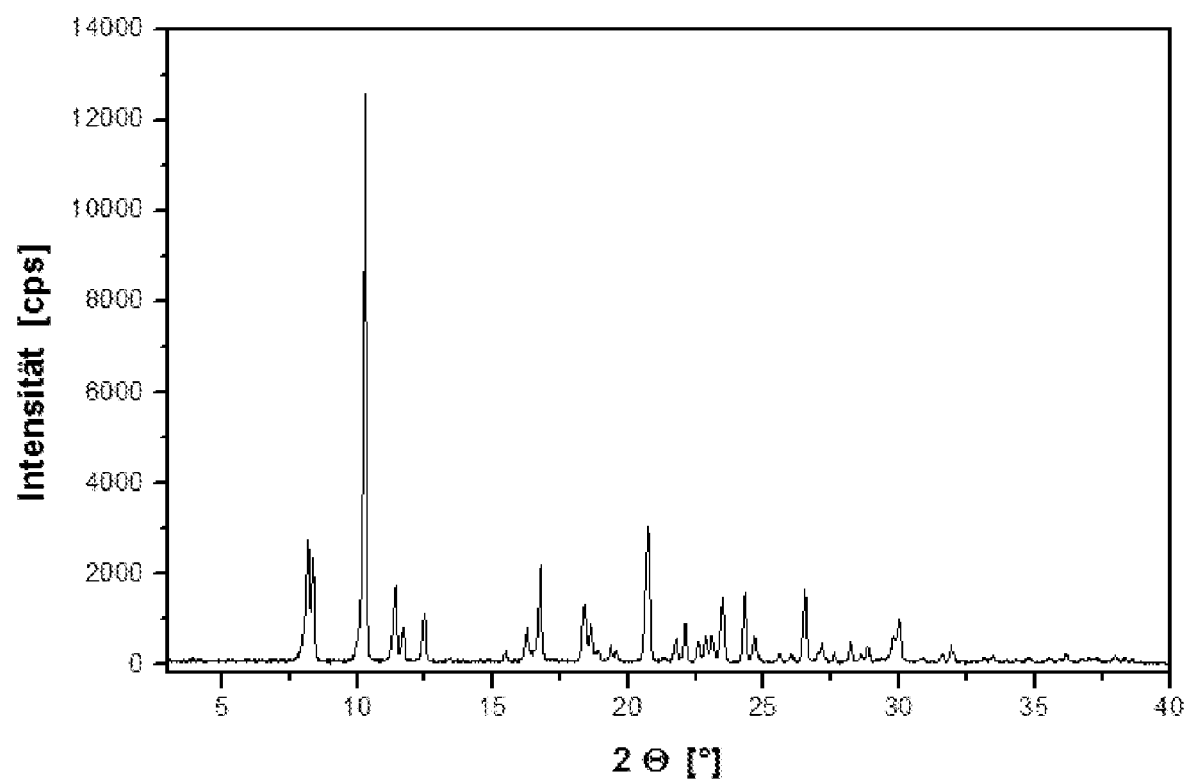
FIG. 1: X-ray powder diagram of the anhydrous form of 1-[(3-cyano-pyridin-2-yl)methyl]-3-methyl-7-(2-butyn-1-yl)-8-(3-(R)-amino-piperidin-1-yl)-xanthine

The following terms are used synonymously: salt with hydrochloric acid and hydrochloride.

The invention therefore relates to the salts of 1-[(3-cyano-pyridin-2-yl)methyl]-3-methyl-7-(2-butyn-1-yl)-8-(3-amino-piperidin-1-yl)-xanthine with hydrochloric acid, as well as the enantiomers thereof, the mixtures and the hydrates thereof. These include for example the mono- and dihydrochloride of 1-[(3-cyano-pyridin-2-yl)methyl]-3-methyl-7-(2-butyn-1-yl)-8-[(R)-3-amino-piperidin-1-yl]-xanthine and 1-[(3-cyano-pyridin-2-yl)methyl]-3-methyl-7-(2-butyn-1-yl)-8-[(S)-3-amino-piperidin-1-yl]-xanthine and the mixtures thereof, including the racemates. The invention further relates to pharmaceutical compositions containing at least one of the above-mentioned salts or hydrates thereof and processes for preparing pharmaceutical compositions.

In view of their ability to inhibit DPP-IV activity, the compounds of general formula I according to the invention and the corresponding pharmaceutically acceptable salts thereof are suitable for influencing any conditions or diseases which can be affected by the inhibition of the DPP-IV activity. It is therefore to be expected that the compounds according to the invention will be suitable for the prevention or treatment of diseases or conditions such as type I and type II diabetes mellitus, prediabetes, reduced glucose tolerance or changes in the fasting blood sugar, diabetic complications (e.g. retinopathy, nephropathy or neuropathies), metabolic acidosis or ketosis, reactive hypoglycaemia, insulin resistance, metabolic syndrome, dyslipidaemias of various origins, arthritis, atherosclerosis and related diseases, obesity, allograft transplantation and osteoporosis caused by calcitonin. In addition, these substances are suitable for preventing B-cell degeneration such as e.g. apoptosis or necrosis of pancreatic B-cells. The substances are also suitable for improving or restoring the function of pancreatic cells and additionally increasing the size and number of pancreatic B-cells. Additionally, on the basis of the role of the glucagon-like peptides such as e.g. GLP-1 and GLP-2 and their link with DPP-IV inhibition, it is expected that the compounds according to the invention will be suitable for achieving, inter alia, a sedative or tranquillising effect, as well as having a favourable effect on catabolic states after operations or hormonal stress responses or possibly reducing mortality and morbidity after myocardial infarction. Moreover, they are suitable for treating any conditions connected with the effects mentioned above and mediated by GLP-1 or GLP-2. The compounds according to the invention may also be used as diuretics or antihypertensives and are suitable for preventing and treating acute kidney failure. The compounds according to the invention may also be used to treat inflammatory complaints of the respiratory tract. They are also suitable for preventing and treating chronic inflammatory bowel diseases such as e.g. irritable bowel syndrome (IBS), Crohn's disease or ulcerative colitis and also pancreatitis. It is also expected that they can be used for all kinds of injury or damage to the gastrointestinal tract such as may occur in colitis and enteritis, for example. Moreover, it is expected that DPP-IV inhibitors and hence the compounds according to the invention can be used to treat infertility or to improve fertility in humans or mammals, particularly if the infertility is connected with insulin resistance or with polycystic ovary syndrome. On the other hand these substances are suitable for influencing sperm motility and are thus suitable for use as male contraceptives. In addition, the substances are suitable for treating growth hormone deficiencies connected with restricted growth, and may reasonably be used for all indications for which growth hormone may be used. The compounds according to the invention are also suitable, on the basis of their inhibitory effect on DPP-IV, for treating various autoimmune diseases such as e.g. rheumatoid arthritis, multiple sclerosis, thyroiditis and Basedow's disease, etc. They may also be used to treat viral diseases and also, for example, in HIV infections, for stimulating blood production, in benign prostatic hyperplasia, gingivitis, as well as for the treatment of neuronal defects and neurodegenerative diseases such as Alzheimer's disease, for example. The compounds described may also be used for the treatment of tumours, particularly for modifying tumour invasion and also metastasisation; examples here are their use in treating T-cell lymphomas, acute lymphoblastic leukaemia, cell-based thyroid carcinomas, basal cell carcinomas or breast cancers. Other indications are stroke, ischaemia of various origins, Parkinson's disease and migraine. In addition, further indications include follicular and epidermal hyperkeratoses, increased keratinocyte proliferation, psoriasis, encephalomyelitis, glomerulonephritis, lipodystrophies, as well as psychosomatic, depressive and neuropsychiatric diseases of all kinds.

The compounds according to the invention may also be used in conjunction with other active substances. Suitable therapeutic agents for such combinations include for example antidiabetic agents such as metformin, sulphonylureas (e.g. glibenclamide, tolbutamide, glimepiride), nateglinide, repaglinide, thiazolidinediones (e.g. rosiglitazone, pioglitazone), PPAR-gamma agonists (e.g. GI 262570) and antagonists, PPAR-gamma/alpha modulators (e.g. KRP 297), PPAR-gamma/alpha/delta modulators, AMPK activators, ACC1 and ACC2 inhibitors, DGAT-inhibitors, SMT3 receptor agonists, 11β-HSD inhibitors, FGF19 agonists or mimetics, alpha-glucosidase inhibitors (e.g. acarbose, voglibose), other DPPIV inhibitors, alpha2 antagonists, insulin and insulin analogues, GLP-1 and GLP-1 analogues (e.g. exendin-4) or amylin. Also, combinations with SGLT2 inhibitors such as T-1095 or KGT-1251 (869682), inhibitors of protein tyrosine phosphatase 1, substances which influence deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, lipid lowering agents, such as HMG-CoA-reductase inhibitors (e.g. simvastatin, atorvastatin), fibrates (e.g. bezafibrate, fenofibrate), nicotinic acid and its derivatives, PPAR-alpha agonists, PPAR-delta agonists, ACAT inhibitors (e.g. avasimibe) or cholesterol absorption inhibitors such as for example ezetimibe, bile acid-binding substances such as for example cholestyramine, inhibitors of ileac bile acid transport, HDL-raising compounds such as for example inhibitors of CETP or regulators of ABC1 or LXRalpha antagonists, LXRbeta agonists or LXRalpha/beta regulators or active substances for the treatment of obesity, such as e.g. sibutramine or tetrahydrolipostatin, dexfenfluramine, axokine, antagonists of the cannabinoid1 receptor, MCH-1 receptor antagonists, MC4 receptor agonists, NPY5 or NPY2 antagonists or β3-agonists such as SB-418790 or AD-9677 as well as agonists of the 5HT2c receptor, are possible.

It is also possible to combine the compounds with drugs for treating high blood pressure such as e.g. AII antagonists or ACE inhibitors, diuretics, 1-blockers, Ca-antagonists, etc., or combinations thereof.

The dosage required to expediently achieve such an effect is, by intravenous route, 1 to 100 mg, preferably 1 to 30 mg, and by oral route 1 to 1000 mg, preferably 1 to 100 mg, in each case 1 to 4 times a day. For this purpose, the compounds of formula I prepared according to the invention, optionally combined with other active substances, may be incorporated together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof into conventional galenic preparations such as plain or coated tablets, capsules, powders, suspensions or suppositories.

Figure 2:
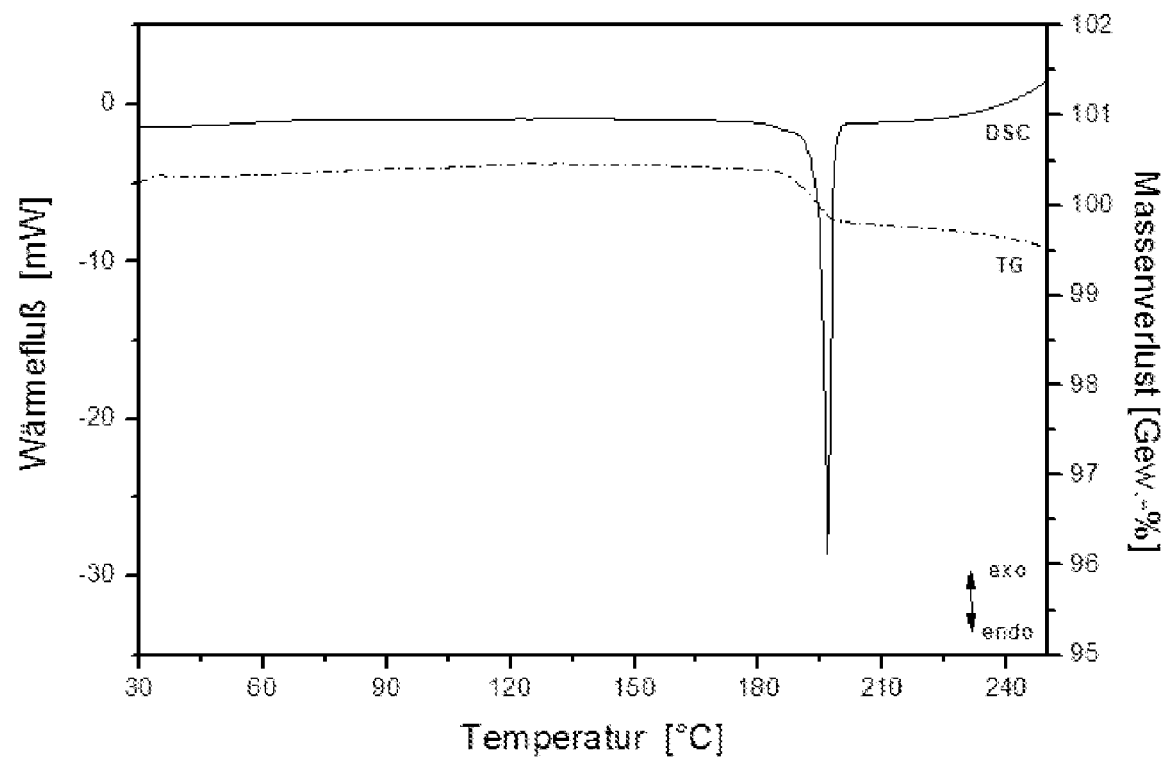
FIG. 2: Thermoanalysis of the anhydrous form of 1-[(3-cyano-pyridin-2-yl)methyl]-3-methyl-7-(2-butyn-1-yl)-8-(3-(R)-amino-piperidin-1-yl)-xanthine
Figure 3:
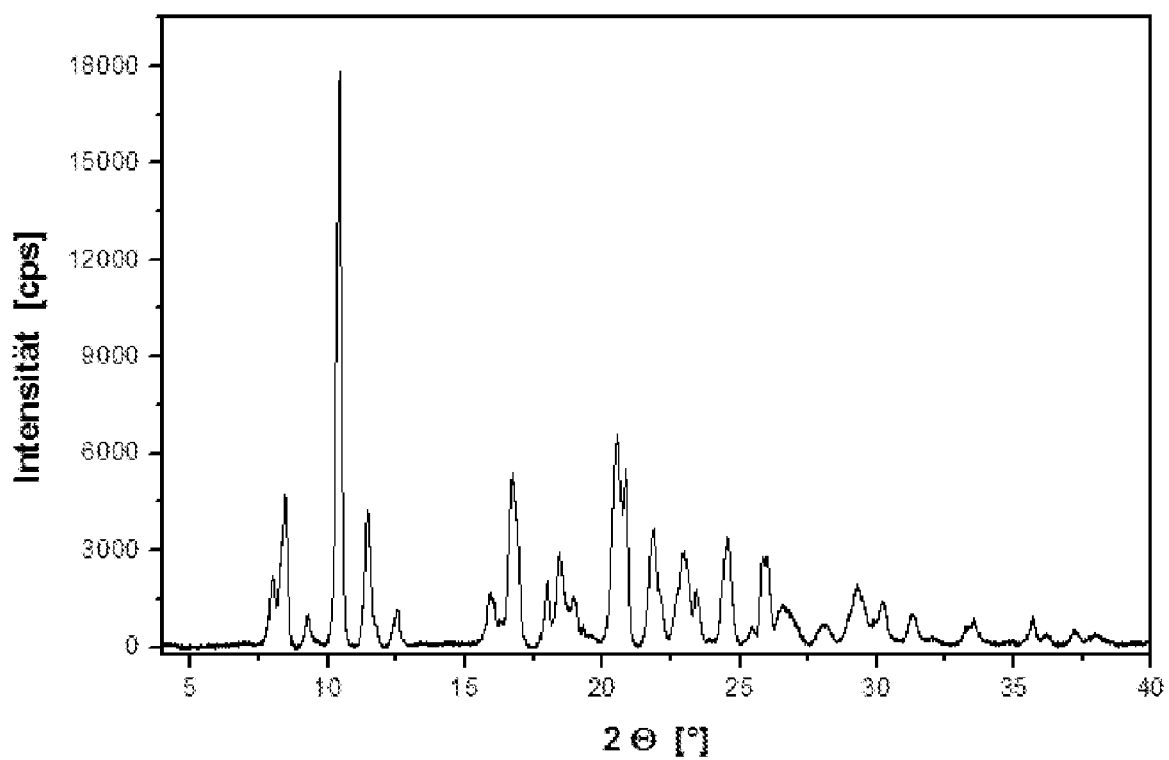
FIG. 3: X-ray powder diagram of the monohydrate of 1-[(3-cyano-pyridin-2-yl)methyl]-3-methyl-7-(2-butyn-1-yl)-8-(3-(R)-amino-piperidin-1-yl)-xanthine
Figure 4:
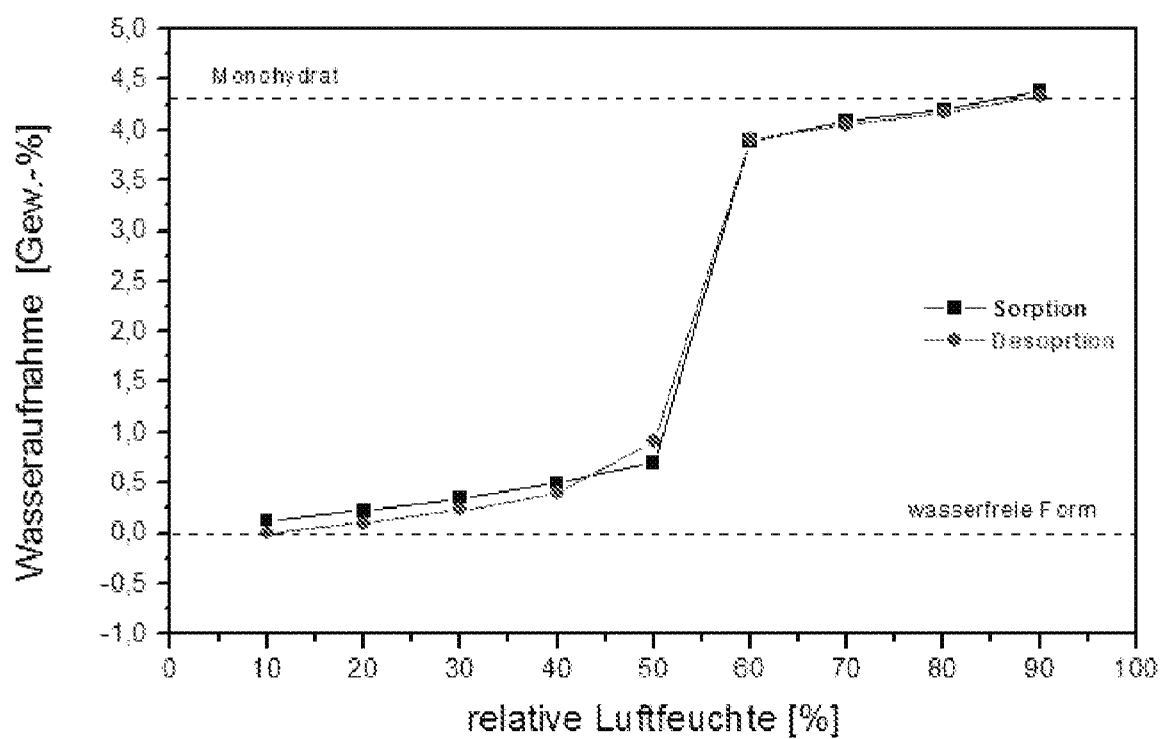
FIG. 4: Absorption characteristics of the free base of 1-[(3-cyano-pyridin-2-yl)methyl]-3-methyl-7-(2-butyn-1-yl)-8-(3-(R)-amino-piperidin-1-yl)-xanthine
Figure 5:
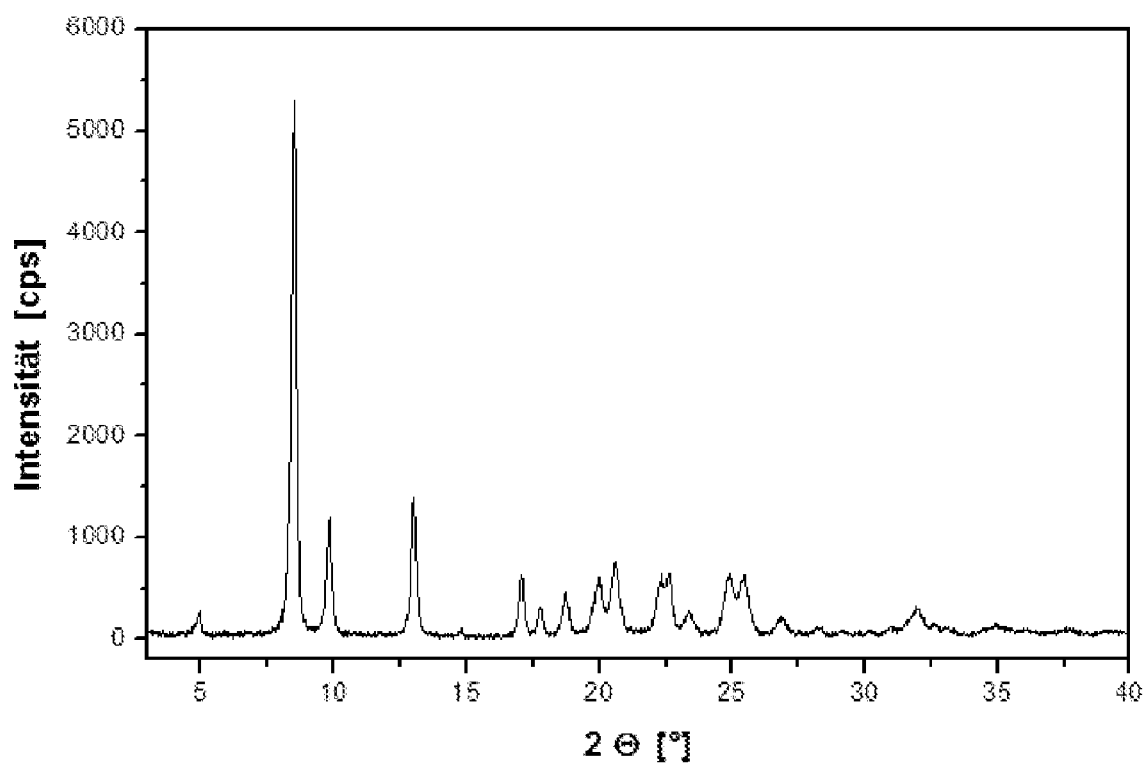
FIG. 5: X-ray powder diagram of 1-[(3-cyano-pyridin-2-yl)methyl]-3-methyl-7-(2-butyn-1-yl)-8-[(R)-3-amino-piperidin-1-yl]-xanthine monohydrochloride
Figure 6:
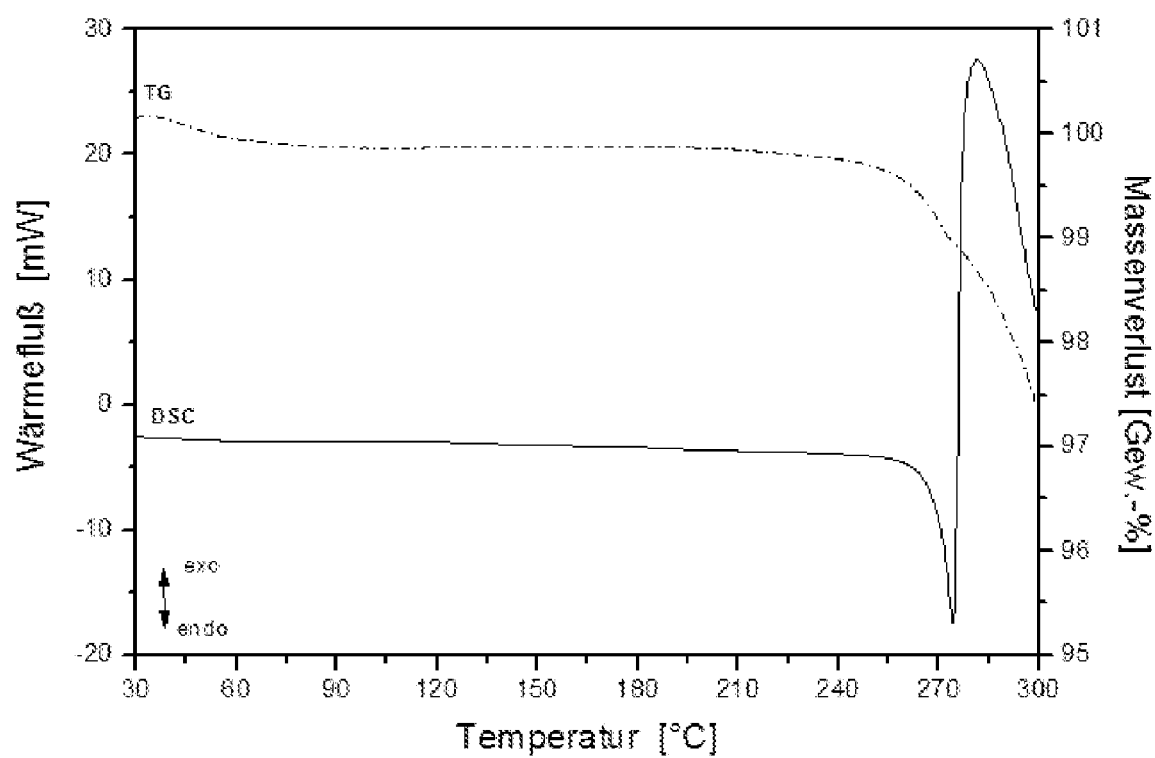
FIG. 6: Thermoanalysis of 1-[(3-cyano-pyridin-2-yl)methyl]-3-methyl-7-(2-butyn-1-yl)-8-[(R)-3-amino-piperidin-1-yl]-xanthine-monohydrochloride
Figure 7:
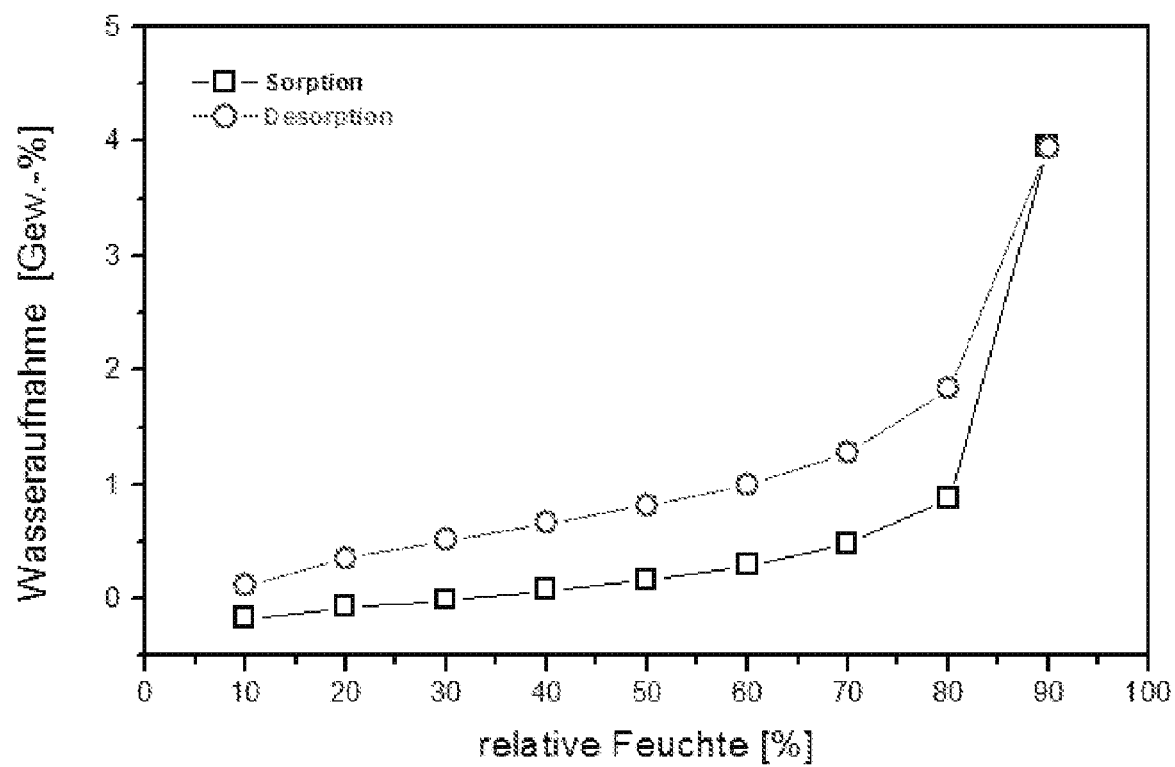
FIG. 7: Absorption characteristics of the monohydrochloride of 1-[(3-cyano-pyridin-2-yl)methyl]-3-methyl-7-(2-butyn-1-yl)-8-(3-(R)-amino-piperidin-1-yl)-xanthine
Figure 8:
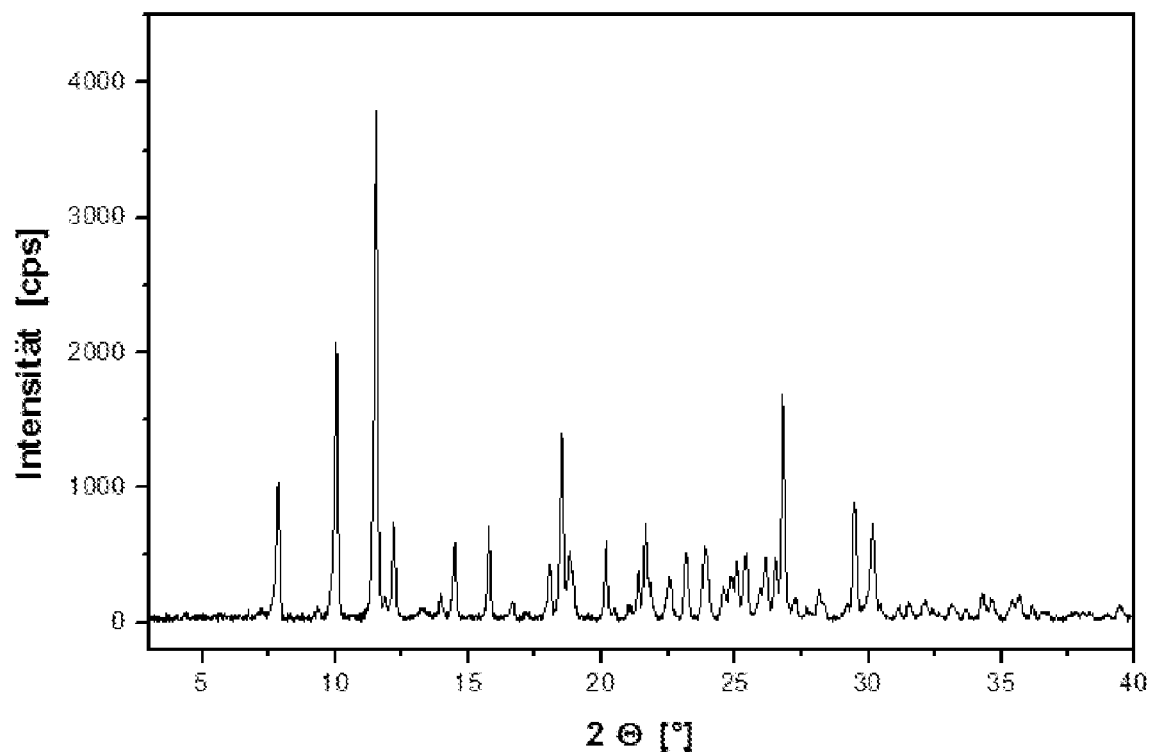
FIG. 8: X-ray powder diagram of 1-[(3-cyano-pyridin-2-yl)methyl]-3-methyl-7-(2-butyn-1-yl)-8-[(R)-3-amino-piperidin-1-yl]-xanthine-dihydrochloride
Figure 9:
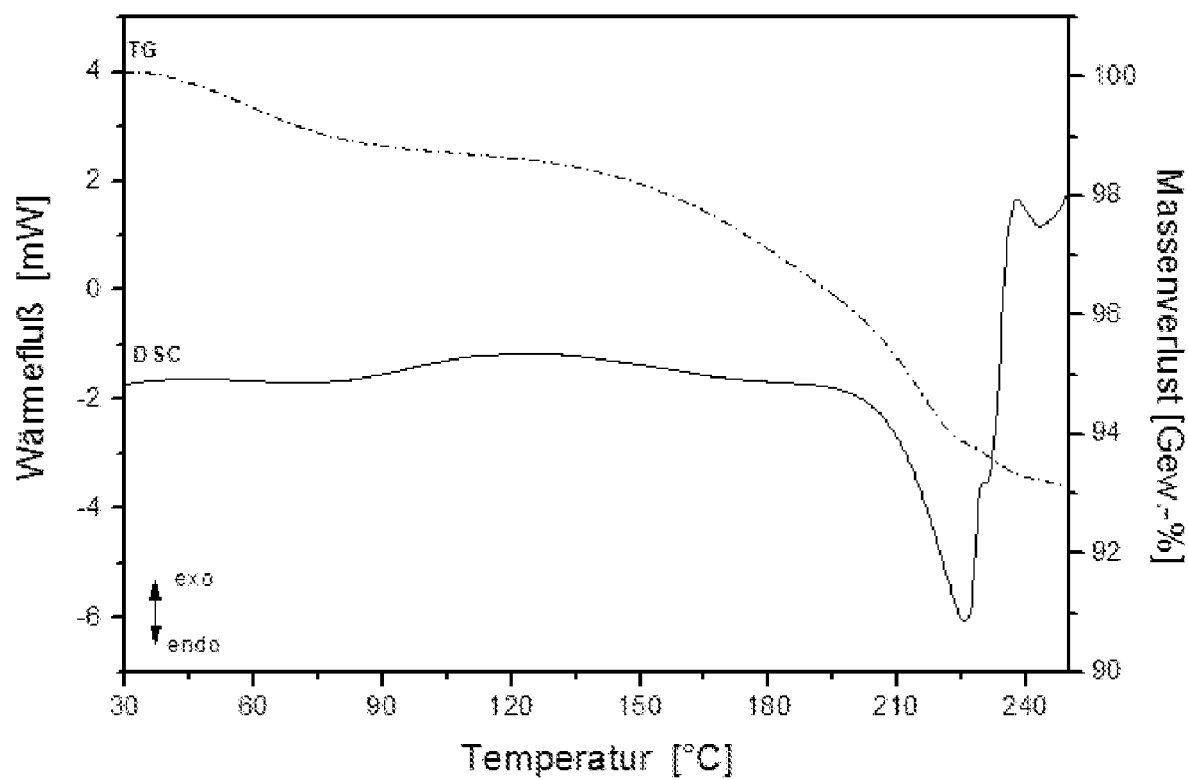
FIG. 9: Thermoanalysis of 1-[(3-cyano-pyridin-2-yl)methyl]-3-methyl-7-(2-butyn-1-yl)-8-[(R)-3-amino-piperidin-1-yl]-xanthine-dihydrochloride
Figure 10:
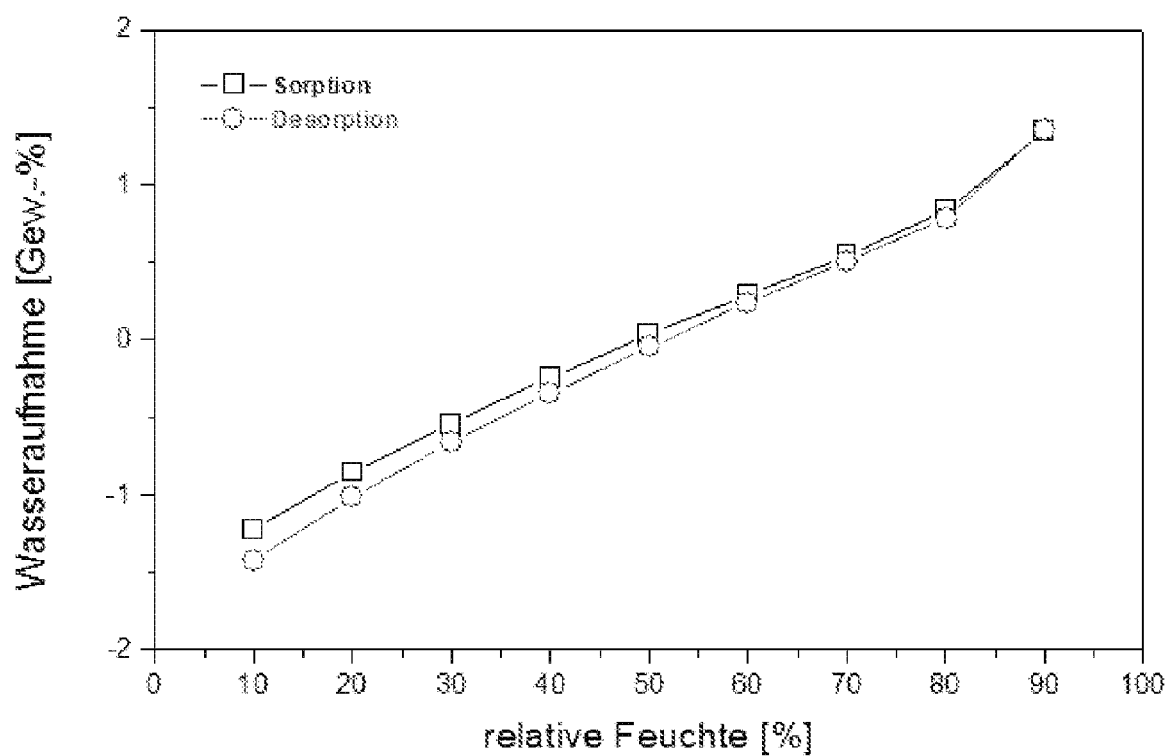
FIG. 10: Absorption characteristics of the dihydrochloride of 1-[(3-cyano-pyridin-2-yl)-methyl]-3-methyl-7-(2-butyn-1-yl)-8-(3-(R)-amino-piperidin-1-yl)-xanthine

FIGS. 1, 3, 5 and 8 show the X-ray powder diagrams of Examples 2 (anhydrous form as well as the monohydrate), 3 and 4; FIGS. 2, 6 and 9 show the thermoanalyses of Examples 2, 3 and 4 and FIGS. 4, 7 and 10 show the absorption characteristics of the free base as well as of the mono- and dihydrochlorides of 1-[(3-cyano-pyridin-2-yl)-methyl]-3-methyl-7-(2-butyn-1-yl)-8-(3-(R)-amino-piperidin-1-yl)-xanthine (Example 2, 3 and 4).

The Examples that follow are intended to illustrate the invention.

EXAMPLE 1

D-tartaric acid salt of the R-enantiomer of 3-(phthalimido)piperidine a. Hydrogenation:

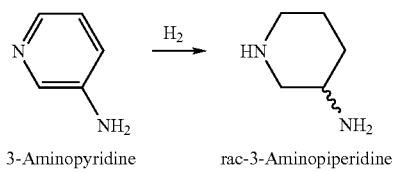

3-Aminopyridine    rac-3-Aminopiperidine 10.00 kg (106.25 mol) of 3-aminopyridine, 500 g of industrial grade activated charcoal and 65 liters of acetic acid are placed in the hydrogenation reactor. 50 g of Nishimura catalyst (a commercially obtainable mixed rhodium/platinum catalyst) are added, suspended in 2.5 liters of acetic acid, and the mixture is rinsed with 2.5 liters of acetic acid. It is hydrogenated at 50° C. and 100 bar excess hydrogen pressure until the hydrogen uptake has stopped and then hydrogenated for a further 30 minutes at 50° C. The catalyst and the activated charcoal are filtered off and washed with 10 liters of acetic acid.

The reaction will also succeed under less drastic pressures.

b. Acylation:

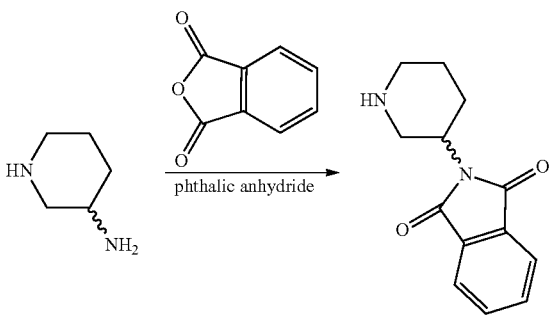

15.74 kg (106.25 mol) phthalic anhydride are placed in the reactor and combined with the filtrate from the hydrogenation. The mixture is rinsed with 7.5 liters of acetic acid, and then the reaction mixture is refluxed, while about 30% of the acetic acid used are distilled off within one hour. The reaction solution is cooled to 90° C.

c. Racemate Cleavage:

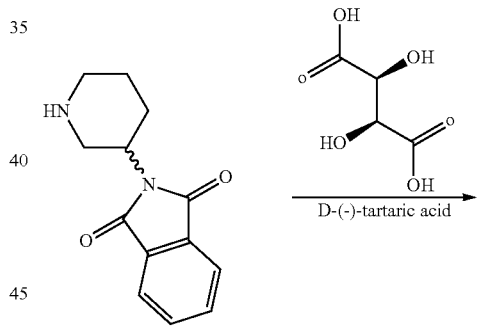

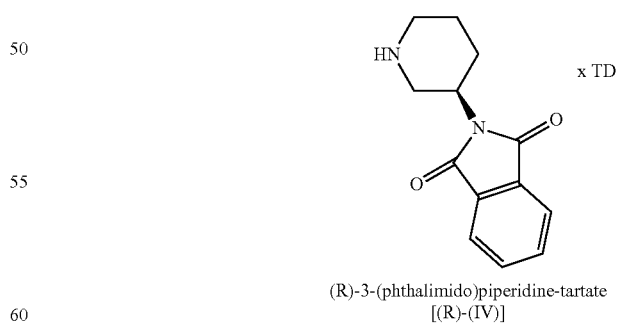

(R)-3-(phthalimido)piperidine-tartate
[(R)-(IV)]

A solution of 11.16 kg D-(−)-tartaric acid (74.38 mol) in 50 liters of absolute ethanol heated to 50° C. is metered at 90° C. into the acylation reaction solution. This is rinsed with 10 liters of absolute ethanol and stirred for 30 minutes at 90° C., during which time the product crystallises out. After cooling to 5° C. the product is centrifuged off and washed with absolute ethanol.

d. Recrystallisation:

The moist crude product is refluxed in a mixture of 50 liters of acetone and 90 liters of water until a solution has formed. Then the mixture is cooled to 5° C., during which time the product crystallises out. The suspension is stirred for 30 minutes at 5° C., the product is centrifuged and finally washed with a mixture of 20 liters of acetone and 10 liters of water. It is dried in the drying cupboard while being rendered inert at 45° C.

Yields: 11.7-12.5 kg

EXAMPLE 2

Preparation of 1-[(3-cyano-pyridin-2-yl)methyl]-3-methyl-7-(2-butyn-1-yl)-8-[(R)-3-amino-piperidin-1-yl]-xanthine base a. 3-cyano-2-(chloromethyl)-pyridine 165.5 g (0.98 mol) 2-hydroxymethyl-3-pyridinecarboxamide are heated together with 270 ml of phosphorus oxychloride for 1 hour at 90-100° C. The reaction mixture is cooled to ambient temperature and then added dropwise to about 800 ml of water at a temperature of 50-60° C. After hydrolysis of the phosphorus oxychloride the mixture is neutralised while being cooled with sodium hydroxide solution, whereupon the product is precipitated. It is filtered off, washed with 300 ml of water and then dried at 35-40° C.

Yield: 122.6 g (82% of theoretical)

b. 1-[(3-cyano-pyridin-2-yl)methyl]-3-methyl-7-(2-butyn-1-yl)-8-bromo-xanthine

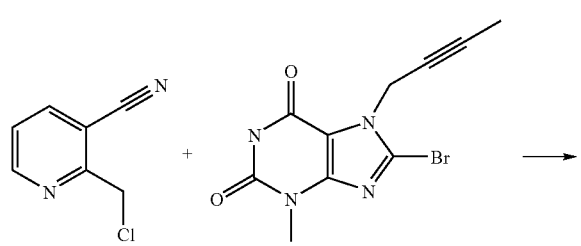

202 g (0.68 mol) 3-methyl-7-(2-butyn-1-yl)-8-bromo-xanthine, 188.5 g (1.36 mol) anhydrous potassium carbonate and 1.68 liters of N-methyl-2-pyrrolidone are placed in the reactor and heated to 70° C. Then 119 g (0.75 mol) 2-chloromethyl-3-cyano-pyridine in 240 ml N-methyl-2-pyrrolidine (NMP) are added dropwise. The contents of the reactor are stirred for 19 hours at 70° C. After the reaction has ended 2.8 liters of water are added to the reaction mixture and it is cooled to 25° C. The product is filtered off, washed with 2 liters of water and dried in the drying cupboard at 70° C. while being rendered inert.

Yield: 257.5 g (91% of theoretical)

c. 1-[(3-cyano-pyridin-2-yl)methyl]-3-methyl-7-(2-butyn-1-yl)-8-(3-(R)-phthalimido-piperidin-1-yl)-xanthine

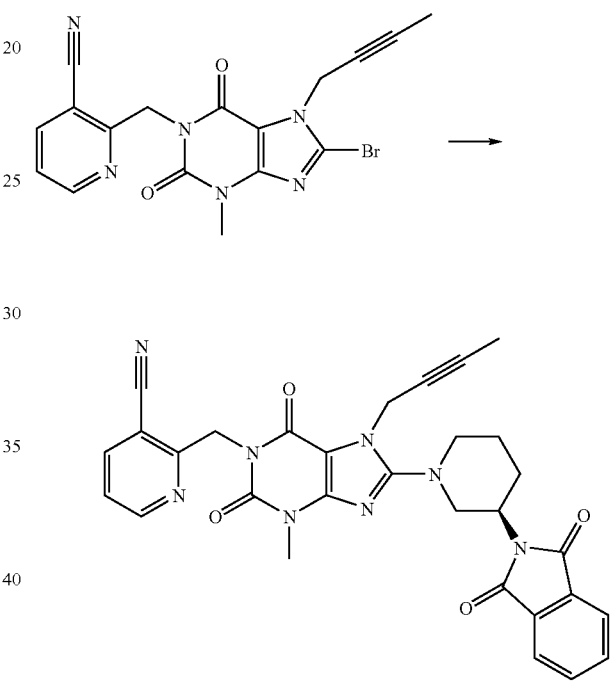

230 g (0.557 mol) 1-[(3-cyano-pyridin-2-yl)methyl]-3-methyl-7-(2-butyn-1-yl)-8-bromo-xanthine, 318 g (0.835 mol) 3-(phthalimido)piperidine D-tartrate and 1.15 liters of N-methyl-2-pyrrolidone are placed in the reactor. The contents of the reactor are heated to 140° C. After reaching this temperature, 478 ml (2.78 mol) diisopropylethylamine are metered in within 20 minutes and the reaction mixture is then stirred for 2 hours at 140° C. Then the reaction mixture is cooled to 75° C. and diluted with 720 ml of methanol. 2.7 liters of water are then added at 68-60° C. and the mixture is cooled to 25° C. The product is filtered off and washed with 2 liters of water. It is dried in the drying cupboard at 70° C. while being rendered inert.

The crude product thus obtained is then stirred into 1 liter of methanol at boiling temperature, filtered hot, washed with 200 ml of methanol and then dried at 70° C. while being rendered inert.

Yield: 275 g (88% of theoretical)

d. 1-[(3-cyano-pyridin-2-yl)methyl]-3-methyl-7-(2-butyn-1-yl)-8-(3-(R)-amino-piperidin-1-yl)-xanthine

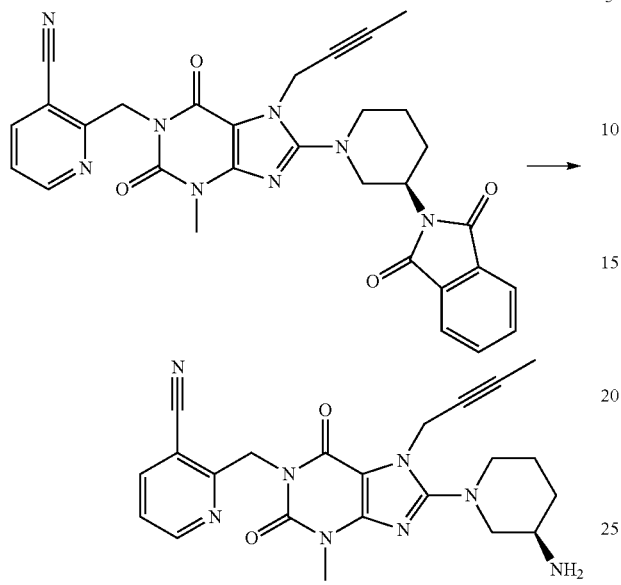

412.5 g (0.733 mol) of 1-[(3-cyano-pyridin-2-yl)methyl]-3-methyl-7-(2-butyn-1-yl)-8-(3-(R)-phthalimido-piperidin-1-yl)-xanthine are heated to 80° C. in 4125 ml of toluene. Then at 75-80° C. 445 ml of ethanolamine (7.33 mol) are added to the suspension. To complete the reaction the mixture is stirred for another 2 hours at 80-85° C., during which time the solids go into solution. Then the phases are separated. The ethanolamine phase is extracted twice with warm toluene (1 liter in each case). The combined toluene phases are washed twice with 2 liters of 75-80° C. warm water on each occasion. The toluene phases are dried with sodium sulphate, filtered and then reduced to a volume of about 430 ml by distillation in vacuo. Then at 50-55° C. 1 liter of tert.-butylmethylether is metered in and the mixture is then cooled to 0-5° C. The product is isolated by filtration, washed with tert.-butylmethylether and dried at 60° C. in the drying cupboard.

Yield: 273.25 g (86.2% of theoretical)
melting point: 188±3° C. (anhydrous form)

The anhydrous form of 1-[(3-cyano-pyridin-2-yl)methyl]-3-methyl-7-(2-butyn-1-yl)-8-(3-(R)-amino-piperidin-1-yl)-xanthine is stable at relative humidities up to about 50%, above 50% r.h. this form takes up about 4% water and changes into a monohydrate, as can clearly be seen from the absorption diagram in FIG. 4. If the relative humidity is subsequently brought back to 50% or less, the anhydrous form is formed again, i.e. the conversion into the monohydrate is totally reversible.

TABLE 1

X-ray reflections with intensities (standardised) for the anhydrous form of 1-[(3-cyano-pyridin-2-yl)methyl]-3-methyl-7-(2-butyn-1-yl)-8-(3-(R)-amino-piperidin-1-yl)-xanthine

| 2Θ [°] | $d_{hkl}$ [Å] | intensity $I/I_o$ [%] |
|---|---|---|
| 8.17 | 10.81 | 22 |
| 8.37 | 10.56 | 19 |
| 10.29 | 8.59 | 100 |
| 11.40 | 7.76 | 14 |
| 11.70 | 7.56 | 6 |
| 12.48 | 7.09 | 9 |
| 14.86 | 5.96 | 1 |
| 15.49 | 5.72 | 2 |
| 16.26 | 5.45 | 7 |
| 16.75 | 5.29 | 18 |
| 18.38 | 4.82 | 11 |
| 18.60 | 4.77 | 7 |
| 18.92 | 4.69 | 3 |
| 19.35 | 4.58 | 3 |
| 19.55 | 4.54 | 2 |
| 20.73 | 4.28 | 24 |
| 21.34 | 4.16 | 1 |
| 21.77 | 4.08 | 4 |
| 22.10 | 4.02 | 7 |
| 22.60 | 3.93 | 4 |
| 22.86 | 3.89 | 5 |
| 23.09 | 3.85 | 5 |
| 23.47 | 3.79 | 11 |
| 24.30 | 3.66 | 12 |
| 24.66 | 3.61 | 5 |
| 25.58 | 3.48 | 2 |
| 26.02 | 3.42 | 2 |
| 26.52 | 3.36 | 13 |
| 27.15 | 3.28 | 3 |
| 27.60 | 3.23 | 2 |
| 28.22 | 3.16 | 4 |
| 28.60 | 3.12 | 2 |
| 28.84 | 3.09 | 3 |
| 29.80 | 3.00 | 5 |
| 30.02 | 2.97 | 8 |

TABLE 2

X-ray reflections with intensities (standardised) for the monohydrate of 1-[(3-cyano-pyridin-2-yl)methyl]-3-methyl-7-(2-butyn-1-yl)-8-(3-(R)-amino-piperidin-1-yl)-xanthine

| 2Θ [°] | dhkl [Å] | intensity $I/I_o$ [%] |
|---|---|---|
| 8.00 | 11.05 | 12 |
| 8.45 | 10.46 | 26 |
| 9.27 | 9.54 | 5 |
| 10.43 | 8.48 | 100 |
| 11.45 | 7.72 | 23 |
| 11.74 | 7.53 | 4 |
| 12.53 | 7.06 | 6 |
| 15.91 | 5.57 | 8 |
| 16.01 | 5.53 | 7 |
| 16.73 | 5.30 | 29 |
| 16.94 | 5.23 | 17 |
| 17.99 | 4.93 | 11 |
| 18.43 | 4.81 | 15 |
| 18.95 | 4.68 | 7 |
| 19.31 | 4.59 | 2 |
| 20.54 | 4.32 | 36 |
| 20.85 | 4.26 | 30 |
| 21.86 | 4.06 | 19 |
| 22.13 | 4.01 | 8 |
| 22.70 | 3.91 | 7 |
| 22.96 | 3.87 | 15 |
| 23.43 | 3.79 | 8 |
| 24.56 | 3.62 | 18 |
| 25.45 | 3.50 | 2 |
| 25.84 | 3.44 | 14 |
| 25.99 | 3.43 | 14 |
| 26.58 | 3.35 | 6 |
| 26.88 | 3.31 | 4 |

TABLE 2-continued

X-ray reflections with intensities (standardised) for the monohydrate of 1-[(3-cyano-pyridin-2-yl)methyl]-3-methyl-7-(2-butyn-1-yl)-8-(3-(R)-amino-piperidin-1-yl)-xanthine

| 2 Θ [°] | dhkl [Å] | intensity I/I$_o$ [%] |
|---|---|---|
| 28.06 | 3.18 | 3 |
| 29.04 | 3.07 | 4 |
| 29.29 | 3.05 | 9 |
| 30.22 | 2.96 | 6 |

EXAMPLE 3

1-[(3-cyano-pyridin-2-yl)methyl]-3-methyl-7-(2-butyn-1-yl)-8-[(R)-3-amino-piperidin-1-yl]-xanthine monohydrochloride 5.00 g of 1-[(3-cyano-pyridin-2-yl)methyl]-3-methyl-7-(2-butyn-1-yl)-8-[(R)-3-amino-piperidin-1-yl]-xanthine base are dissolved in 50 ml of methanol. Then 3.0 ml of a 3.9 molar solution of hydrogen chloride in isopropanol are added. The solvent is distilled off and the residue is suspended in 40 ml ethyl acetate and refluxed, during which time a precipitate is formed. It is cooled to ambient temperature, the precipitate is filtered off and washed with a little ethyl acetate and dried.

The product is then recrystallised from absolute ethanol.
Yield: 2.7 g (50% of theory)
melting point: 265±5° C. (with decomposition)

The monohydrochloride exhibits less marked hygroscopic characteristics; there is no reversible change into a hydrate phase as is observed with the free base between 50 and 60% r.h. (see the absorption characteristics of the monohydrochloride in FIG. 7). Also, the monohydrochloride only absorbs water at very high relative humidities (>80% r.h.). Humidity-dependent X-ray powder images show that there is no phase change above 80% r.h. for the monohydrochloride.

TABLE 3

X-ray reflections with intensities (standardised) for the anhydrous form of 1-[(3-cyano-pyridin-2-yl)methyl]-3-methyl-7-(2-butyn-1-yl)-8-[(R)-3-amino-piperidin-1-yl]-xanthine monohydrochloride

| 2 Θ [°] | d$_{hkl}$ [Å] | Intensity I/I$_o$ [%] |
|---|---|---|
| 17.95 | 4.92 | 5 |
| 10.38 | 8.51 | 100 |
| 8.99 | 9.83 | 22 |
| 6.80 | 13.01 | 26 |
| 5.97 | 14.82 | 1 |
| 5.19 | 17.07 | 12 |
| 4.99 | 17.78 | 5 |
| 4.74 | 18.72 | 8 |
| 4.44 | 20.00 | 10 |
| 4.31 | 20.60 | 13 |
| 3.98 | 22.33 | 10 |
| 3.93 | 22.61 | 11 |
| 3.80 | 23.38 | 4 |
| 3.57 | 24.91 | 11 |
| 3.50 | 25.43 | 11 |
| 3.32 | 26.87 | 4 |
| 3.15 | 28.35 | 2 |
| 2.96 | 30.20 | 1 |
| 2.89 | 30.97 | 2 |
| 2.80 | 31.92 | 5 |
| 2.74 | 32.63 | 2 |
| 2.57 | 34.89 | 2 |

EXAMPLE 4

1-[(3-cyano-pyridin-2-yl)methyl]-3-methyl-7-(2-butyn-1-yl)-8-[(R)-3-amino-piperidin-1-yl]-xanthine-dihydrochloride 1-[(3-cyano-pyridin-2-yl)methyl]-3-methyl-7-(2-butyn-1-yl)-8-[(R)-3-amino-piperidin-1-yl]-xanthine base (1.00 g; 2.31 mmol) are dissolved in 9.5 ml abs. ethanol and 0.5 ml methyl-tert.-butylether at boiling temperature. Then 1.2 ml of a 3.9 molar solution of hydrogen chloride in isopropanol is added. A precipitate is formed. After cooling to ambient temperature the mixture is filtered, washed with a little MTBE and dried.

Yield: 1.04 g (89.0% of theory)
Melting point: 205±5° C. (with decomposition); above about 150° C. gaseous HCl is given off.

The dihydrochloride also exhibits unremarkable hygroscopic behaviour; there is no reversible change into a hydrate phase as observed with the free base between 50 and 60% r.h. (see the absorption characteristics of the dihydrochloride in FIG. 10). The dihydrochloride takes up a certain amount of water continuously over the whole range of relative humidities. Humidity-dependent X-ray powder images show that there is no phase change in the humidity range from 10-90 r.h.

TABLE 4

X-ray reflections with intensities (standardised) for the anhydrous form of 1-[(3-cyano-pyridin-2-yl)methyl]-3-methyl-7-(2-butyn-1-yl)-8-[(R)-3-amino-piperidin-1-yl]-xanthine-dihydrochloride

| 2 Θ [°] | d$_{hkl}$ [Å] | intensity I/I$_o$ [%] |
|---|---|---|
| 7.20 | 12.26 | 3 |
| 7.86 | 11.24 | 27 |
| 9.34 | 9.46 | 3 |
| 10.04 | 8.81 | 54 |
| 11.53 | 7.67 | 100 |
| 11.87 | 7.45 | 5 |
| 12.20 | 7.25 | 19 |
| 13.25 | 6.68 | 2 |
| 13.97 | 6.33 | 5 |
| 14.47 | 6.12 | 15 |
| 15.77 | 5.61 | 18 |
| 16.65 | 5.32 | 4 |
| 17.15 | 5.17 | 2 |
| 18.05 | 4.91 | 11 |
| 18.50 | 4.79 | 37 |
| 18.80 | 4.72 | 14 |
| 20.16 | 4.40 | 15 |
| 20.46 | 4.34 | 2 |
| 21.03 | 4.22 | 3 |
| 21.36 | 4.16 | 10 |
| 21.64 | 4.10 | 18 |
| 22.54 | 3.94 | 9 |
| 23.17 | 3.84 | 13 |
| 23.90 | 3.72 | 15 |
| 24.57 | 3.62 | 7 |
| 24.86 | 3.58 | 9 |
| 25.06 | 3.55 | 11 |
| 25.39 | 3.50 | 13 |
| 25.95 | 3.43 | 6 |
| 26.14 | 3.41 | 13 |
| 26.52 | 3.36 | 12 |
| 26.79 | 3.32 | 43 |
| 27.24 | 3.27 | 4 |
| 27.66 | 3.22 | 3 |
| 28.15 | 3.17 | 6 |
| 29.22 | 3.05 | 3 |
| 29.48 | 3.03 | 23 |
| 30.16 | 2.96 | 18 |

The melting points were determined by DSC, using an apparatus supplied by Mettler-Toledo (type: DSC 821). The melting temperature used was the temperature of onset of the corresponding melt peak in the DSC diagram. Heating rates of 10 K/min were used and the experiments were carried out under a nitrogen atmosphere.

The X-ray powder diagrams, with one exception, were recorded using an STOE Stadi P X-ray powder diffractometer. This diffractometer operates with $CuK_{\alpha1}$ radiation (gamma=1.5406 Angstroms) and a location-sensitive detector. The X-ray generator was operated at 40 mA and 40 kV.

The X-ray powder diagram of the monohydrate of the free base was recorded with a Bruker D8 Advance X-ray powder diffractometer on which a special air humidity cell made by MRI had been placed. The diagram was recorded at about 72% r.h. The Bruker D8 Advance operates with $CuK_{\alpha}$ radiation (gamma=1.5418 Angstroms) and also a location-sensitive detector. The X-ray generator was operated at 30 mA and 40 kV.

EXAMPLE 5

Coated Tablets Containing 75 mg of Active Substance

1 Tablet Core Contains:

| | |
|---|---|
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinyl pyrrolidone, hydroxypropylmethylcellulose and half the specified amount of magnesium stearate. Blanks about 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

weight of core: 230 mg die: 9 mm, convex

The tablet cores thus produced are coated with a film consisting essentially of hydroxypropylmethylcellulose. The finished film-coated tablets are polished with beeswax.

Weight of coated tablet: 245 mg.

EXAMPLE 6

Tablets Containing 100 mg of Active Substance

Composition:
1 Tablet Contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg

Diameter: 10 mm, biplanar, facetted on both sides and notched on one side.

EXAMPLE 7

Tablets Containing 150 mg of Active Substance

Composition:
1 Tablet Contains:

| | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm.

The granules, dried at 45° C., are passed through the same screen again and mixed with the specified amount of magnesium stearate. Tablets are pressed from the mixture.

Weight of tablet: 300 mg die: 10 mm, flat

EXAMPLE 8

Hard Gelatine Capsules Containing 150 mg of Active Substance

1 Capsule Contains:

| | | |
|---|---|---|
| active substance | | 150.0 mg |
| corn starch (dried) | approx. | 180.0 mg |
| lactose (powdered) | approx. | 87.0 mg |
| magnesium stearate | | 3.0 mg |
| | approx. | 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg

Capsule shell: size 1 hard gelatine capsule

EXAMPLE 9

Suppositories Containing 150 mg of Active Substance

1 Suppository Contains:

| | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

EXAMPLE 10

Suspension Containing 50 mg of Active Substance 100 ml of Suspension Contain:

| | |
|---|---|
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavouring | 0.30 g |
| dist. water | ad 100 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

5 ml of suspension contain 50 mg of active substance.

EXAMPLE 11

Ampoules Containing 10 mg Active Substance

Composition:

| | |
|---|---|
| active substance | 10.0 mg |
| 0.01 N hydrochloric acid | q.s. |
| double-distilled water | ad 2.0 ml |

Preparation:

The active substance is dissolved in the necessary amount of 0.01 N HCl, made isotonic with common salt, filtered sterile and transferred into 2 ml ampoules.

EXAMPLE 12

Ampoules Containing 50 mg of Active Substance

Composition:

| | |
|---|---|
| active substance | 50.0 mg |
| 0.01 N hydrochloric acid | q.s. |
| double-distilled water | ad 10.0 ml |

Preparation:

The active substance is dissolved in the necessary amount of 0.01 N HCl, made isotonic with common salt, filtered sterile and transferred into 10 ml ampoules.

What is claimed is:

1. A compound which is the monohydrochloride or dihydrochloride salt of 1-[(3-cyano-pyridin-2-yl)methyl]-3-methyl-7-(2-butyn-1-yl)-8-(3-(R)-amino-piperidin-1-yl)-xanthine in crystalline anhydrous form.

2. A compound which is the monohydrochloride salt of 1-[(3-cyano-pyridin-2-yl)methyl]-3-methyl-7-(2-butyn-1-yl)-8-(3-(R)-amino-piperidin-1-yl)-xanthine having a melting point of 260° C. to 270° C.

3. A compound which is the monohydrochloride salt of 1-[(3-cyano-pyridin-2-yl)methyl]-3-methyl-7-(2-butyn-1-yl)-8-(3-(R)-amino-piperidin-1-yl)-xanthine, and wherein an x-ray powder diagram of the monohydrochloride comprises the characteristic values $2\theta=8.51°$, 9.83°, 13.01°, 17.07°, 20.00°, 20.60°, 22.33°, 22.61°, 24.91°, and 25.43° with intensities of at least about 10%.

4. A compound which is the dihydrochloride salt of 1-[(3-cyano-pyridin-2-yl)methyl]-3-methyl-7-(2-butyn-1-yl)-8-(3-(R)-amino-piperidin-1-yl)-xanthine having a melting point of 200° C. to 210° C.

5. A compound which is the dihydrochloride salt of 1-[(3-cyano-pyridin-2-yl)methyl]-3-methyl-7-(2-butyn-1-yl)-8-(3-(R)-amino-piperidin-1-yl)-xanthine, and wherein an x-ray powder diagram of the dihydrochloride comprises the characteristic values $2\theta=7.86°$, 10.04°, 11.53°, 12.20°, 15.77°, 18.50°, 21.64°, 26.79°, 29.48°, and 30.16° with intensities of at least about 18%.

6. A pharmaceutical composition comprising an excipient and a compound which is the monohydrochloride or dihydrochloride salt of 1-[(3-cyano-pyridin-2-yl)methyl]-3-methyl-7-(2-butyn-1-yl)-8-(3-(R)-amino-piperidin-1-yl)-xanthine in crystalline anhydrous form.

7. A pharmaceutical composition comprising an excipient and a compound which is the monohydrochloride salt of 1-[(3-cyano-pyridin-2-yl)methyl]-3-methyl-7-(2-butyn-1-yl)-8-(3-(R)-amino-piperidin-1-yl)-xanthine having a melting point of 260° C. to 270° C.

8. A pharmaceutical composition comprising an excipient and a compound which is the monohydrochloride salt of 1-[(3-cyano-pyridin-2-yl)methyl]-3-methyl-7-(2-butyn-1-yl)-8-(3-(R)-amino-piperidin-1-yl)-xanthine, and wherein an x-ray powder diagram of the monohydrochloride comprises the characteristic values $2\theta=8.51°$, 9.83°, 13.01°, 17.07°, 20.00°, 20.60°, 22.33°, 22.61°, 24.91°, and 25.43° with intensities of at least about 10%.

9. A pharmaceutical composition comprising an excipient and a compound which is the dihydrochloride salt of 1-[(3-cyano-pyridin-2-yl)methyl]-3-methyl-7-(2-butyn-1-yl)-8-(3-(R)-amino-piperidin-1-yl)-xanthine having a melting point of 200° C. to 210° C.

10. A pharmaceutical composition comprising an excipient and a compound which is the dihydrochloride salt of 1-[(3-cyano-pyridin-2-yl)methyl]-3-methyl-7-(2-butyn-1-yl)-8-(3-(R)-amino-piperidin-1-yl)-xanthine, and wherein an x-ray powder diagram of the dihydrochloride comprises the characteristic values 2θ=7.86°, 10.04°, 11.53°, 12.20°, 15.77°, 18.50°, 21.64°, 26.79°, 29.48°, and 30.16° with intensities of at least about 18%.

11. A method for treating Type II diabetes mellitus or obesity in a mammal comprising administering to a mammal in need thereof a compound which is the monohydrochloride or dihydrochloride salt of 1-[(3-cyano-pyridin-2-yl)methyl]-3-methyl-7-(2-butyn-1-yl)-8-(3-(R)-amino-piperidin-1-yl)-xanthine in crystalline anhydrous form.

12. A method for treating Type II diabetes mellitus or obesity in a mammal comprising administering to a mammal in need thereof a compound which is the monohydrochloride salt of 1-[(3-cyano-pyridin-2-yl)methyl]-3-methyl-7-(2-butyn-1-yl)-8-(3-(R)-amino-piperidin-1-yl)-xanthine having a melting point of 260° C. to 270° C.

13. A method for treating Type II diabetes mellitus or obesity in a mammal comprising administering to a mammal in need thereof a compound which is the monohydrochloride salt of 1-[(3-cyano-pyridin-2-yl)methyl]-3-methyl-7-(2-butyn-1-yl)-8-(3-(R)-amino-piperidin-1-yl)-xanthine, and wherein an x-ray powder diagram of the monohydrochloride comprises the characteristic values 2θ=8.51°, 9.83°, 13.01°, 17.07°, 20.00°, 20.60°, 22.33°, 22.61°, 24.91°, and 25.43° with intensities of at least about 10%.

14. A method for treating Type II diabetes mellitus or obesity in a mammal comprising administering to a mammal in need thereof a compound which is the dihydrochloride salt of 1-[(3-cyano-pyridin-2-yl)methyl]-3-methyl-7-(2-butyn-1-yl)-8-(3-(R)-amino-piperidin-1-yl)-xanthine having a melting point of 200° C. to 210° C.

15. A method for treating Type II diabetes mellitus or obesity in a mammal comprising administering to a mammal in need thereof a compound which is the dihydrochloride salt of 1-[(3-cyano-pyridin-2-yl)methyl]-3-methyl-7-(2-butyn-1-yl)-8-(3-(R)-amino-piperidin-1-yl)-xanthine, and wherein an x-ray powder diagram of the dihydrochloride comprises the characteristic values 2θ=7.86°, 10.04°, 11.53°, 12.20°, 15.77°, 18.50°, 21.64°, 26.79°, 29.48°, and 30.16° with intensities of at least about 18%.

16. The compound of claim 2, wherein the (R) configuration compound is isolated from the corresponding (S) configuration compound.

17. The compound of claim 3, wherein the (R) configuration compound is isolated from the corresponding (S) configuration compound.

18. The compound of claim 4, wherein the (R) configuration compound is isolated from the corresponding (S) configuration compound.

19. The compound of claim 5, wherein the (R) configuration compound is isolated from the corresponding (S) configuration compound.

20. The monohydrochloride compound of claim 2, wherein an x-ray powder diagram of the monohydrochloride compound comprises the characteristic values 2θ=8.51°, 9.83°, 13.01°, 17.07°, 20.00°, 20.60°, 22.33°, 22.61°, 24.91°, and 25.43° with intensities of at least about 10%.

21. The dihydrochloride compound of claim 4, wherein an x-ray powder diagram of the dihydrochloride compound comprises the characteristic values 2θ=7.86°, 10.04°, 11.53°, 12.20°, 15.77°, 18.50°, 21.64°, 26.79°, 29.48°, and 30.16° with intensities of at least about 18%.

\* \* \* \* \*